(12) United States Patent
Kosugi et al.

(10) Patent No.: US 9,027,574 B2
(45) Date of Patent: May 12, 2015

(54) CLEANING/DISINFECTING APPARATUS

(71) Applicant: Olympus Medical Systems Corp., Tokyo (JP)

(72) Inventors: Aiko Kosugi, Sagamihara (JP); Michifumi Yoshie, Hino (JP); Akihisa Ogawa, Hachioji (JP); Masahiko Tomita, Hachioji (JP); Yoshitomo Yaguchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/187,433

(22) Filed: Feb. 24, 2014

(65) Prior Publication Data
US 2014/0166059 A1    Jun. 19, 2014

Related U.S. Application Data

(63) Continuation of application No. PCT/JP2013/065340, filed on Jun. 3, 2013.

(30) Foreign Application Priority Data

Aug. 31, 2012   (JP) .................................. 2012-191181

(51) Int. Cl.
| | |
|---|---|
| *A61B 1/00* | (2006.01) |
| *A61B 19/00* | (2006.01) |
| *B08B 9/02* | (2006.01) |
| *B08B 13/00* | (2006.01) |
| *A61B 1/12* | (2006.01) |

(52) U.S. Cl.
CPC ................. *B08B 13/00* (2013.01); *A61B 1/123* (2013.01); *A61B 1/00057* (2013.01); *A61B 1/00059* (2013.01); *A61B 1/00119* (2013.01); *A61B 1/00128* (2013.01); *A61B 1/125* (2013.01); *A61B 2019/343* (2013.01); *B08B 9/02* (2013.01); *A61B 19/34* (2013.01); *A61B 2019/448* (2013.01)

(58) Field of Classification Search
USPC ......................................................... 134/113
See application file for complete search history.

(56) References Cited

U.S. PATENT DOCUMENTS

2007/0154371 A1* 7/2007 Lin et al. ........................ 422/300
2010/0071736 A1   3/2010 Watanabe et al.

FOREIGN PATENT DOCUMENTS

| JP | 04-017835 A | 1/1992 |
|---|---|---|
| JP | 11-276434 A | 10/1999 |
| JP | 2008-264312 A | 11/2008 |

(Continued)

*Primary Examiner* — Joseph L Perrin
*Assistant Examiner* — Levon J Shahinian
(74) *Attorney, Agent, or Firm* — Scully, Scott, Murphy & Presser, P.C.

(57) ABSTRACT

A cleaning/disinfecting apparatus includes: a plurality of attachment portions for attaching an endoscope; a cleaning/disinfecting portion that communicates with the plurality of attachment portions and can execute different types of cleaning/disinfection menus for the respective attachment portions; and an endoscope information reading portion that reads endoscope information from the endoscope. Also, the cleaning/disinfecting apparatus includes: a control portion that determines a cleaning/disinfection menu based on the read endoscope information and outputs attachment portion identifying information for identifying an attachment portion for executing the determined cleaning/disinfection menu; and a notifying portion that notifies the attachment portion identifying information outputted from the control portion.

4 Claims, 31 Drawing Sheets

(56) References Cited

FOREIGN PATENT DOCUMENTS

| | | |
|---|---|---|
| JP | 2009-136355 A | 6/2009 |
| JP | 2009-136492 A | 6/2009 |
| JP | 2009-172055 A | 8/2009 |
| JP | 2010-017411 A | 1/2010 |
| JP | 2010-075267 A | 4/2010 |

* cited by examiner

| ID CHIP ||||
|---|---|---|---|
| No. | TUBE INFORMATION | INDEX | REMARKS |
| 1 | MAJ○○○○ | — | WATER LEAKAGE |
| 2 | MAJ○○○○ | — | HOLDER |
| 3 | MAJ○○○○ | 0~29 | TUBE |
| 4 | MAJ○○○○ | 0~29 | TUBE |
| 5 | MAJ○○○○ | 0~29 | TUBE |
| 6 | MAJ○○○○ | 0~29 | TUBE |
| 7 | MAJ○○○○ | 0~29 | TUBE |
| 8 | MAJ○○○○ | 0~29 | TUBE |

FIG.4

| TABLE | | | |
|---|---|---|---|
| INDEX | PART 1 | PART 2 | PART 3 |
| 0 | B | | |
| 1 | B | B | |
| 2 | B | B | S |
| 3 | B | B | A/W |
| 4 | B | B | JET/K/AUXILIARY WATER FEEDING |
| 5 | B | C | |
| 6 | B | C | S |
| 7 | B | C | A/W |
| 8 | B | C | JET/K/AUXILIARY WATER FEEDING |
| 9 | B | A/W | |
| 10 | B | A/W | A/W |
| 11 | B | A/W | JET/K/AUXILIARY WATER FEEDING |
| 12 | B | JET/K/AUXILIARY WATER FEEDING | |
| 13 | B | JET/K/AUXILIARY WATER FEEDING | JET/K/AUXILIARY WATER FEEDING |
| 14 | S | | |
| 15 | S | S | |
| 16 | S | S | A/W |
| 17 | S | S | JET/K/AUXILIARY WATER FEEDING |
| 18 | S | A/W | |
| 19 | S | A/W | A/W |
| 20 | S | A/W | JET/K/AUXILIARY WATER FEEDING |
| 21 | S | JET/K/AUXILIARY WATER FEEDING | |
| 22 | S | JET/K/AUXILIARY WATER FEEDING | JET/K/AUXILIARY WATER FEEDING |
| 23 | A/W | | |
| 24 | A/W | A/W | |
| 25 | A/W | A/W | JET/K/AUXILIARY WATER FEEDING |
| 26 | A/W | JET/K/AUXILIARY WATER FEEDING | |
| 27 | A/W | JET/K/AUXILIARY WATER FEEDING | JET/K/AUXILIARY WATER FEEDING |
| 28 | JET/K/AUXILIARY WATER FEEDING | | |
| 29 | JET/K/AUXILIARY WATER FEEDING | JET/K/AUXILIARY WATER FEEDING | |

| TUBE INFORMATION DISPLAY EXAMPLE (TWO-CHANNEL SCOPE) | | |
|---|---|---|
| ATTACHMENT PORTION NAME | PART | TUBE INFORMATION |
| WHITE 1 | B | MAJ2500① |
| WHITE 2 | B | MAJ2500② |
| VIOLET 1 | S | MAJ2500③ |
| VIOLET 2 | S | — |
| LIGHT BLUE 1 | A/W | MAJ3000 |
| LIGHT BLUE 2 | A/W | — |
| GREEN 1 | JET/K/AUXILIARY WATER FEEDING | MAJ4000 |
| GREEN 2 | JET/K/AUXILIARY WATER FEEDING | — |
| BLACK 1 | WATER LEAKAGE | MAJ3500 |
| BLACK 2 | WATER LEAKAGE | — |
| HOLDER | HOLDER | MAJ8000 |

B: Biopsy

S: Suction

A/W: Air/Water

JET/K/AUXILIARY WATER FEEDING
Jet CONDUIT/FORCEPS ELEVATOR
/AUXILIARY WATER FEEDING

FIG.6

| STEPS IN CLEANING /DISINFECTION MENU | WATER LEAKAGE CHECK | CLEANING TIME PERIOD | RINSING TIME PERIOD | DISINFECTION | RINSING TIME PERIOD | AIR FEEDING TIME PERIOD | ALCOHOL FLUSH |
|---|---|---|---|---|---|---|---|
| CLEANING/DISINFECTION MENU SUITABLE FOR ENDOSCOPE 100a | PROGRAM FOR LARGE CAPACITY | LONG | LONG | NORMAL | LONG | LONG | LARGE AMOUNT |
| CLEANING/DISINFECTION MENU SUITABLE FOR ENDOSCOPE 100b | PROGRAM FOR SMALL CAPACITY | SHORT | SHORT | NORMAL | SHORT | SHORT | SMALL AMOUNT |

SEQUENCE OF CLEANING ⟶
/DISINFECTION MENU

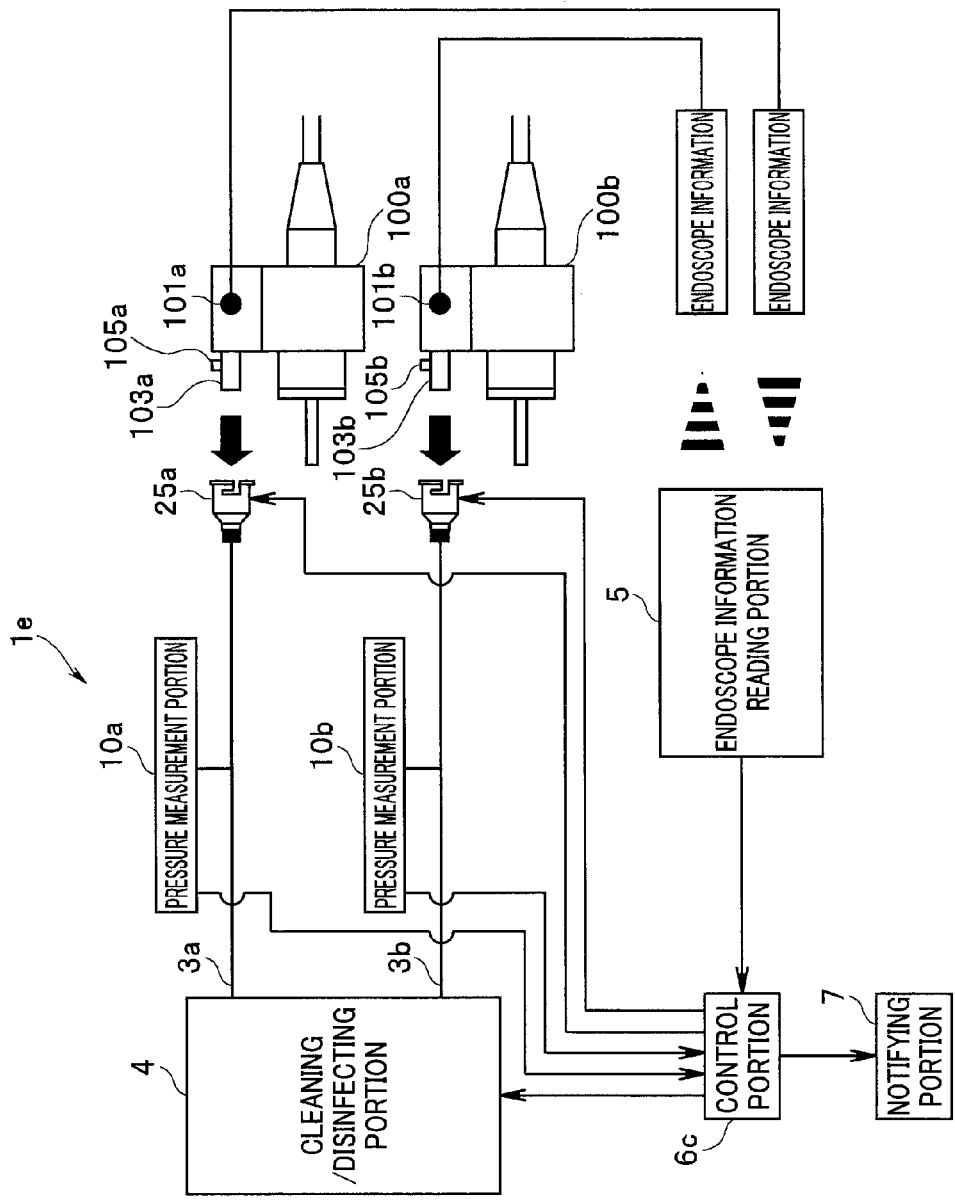

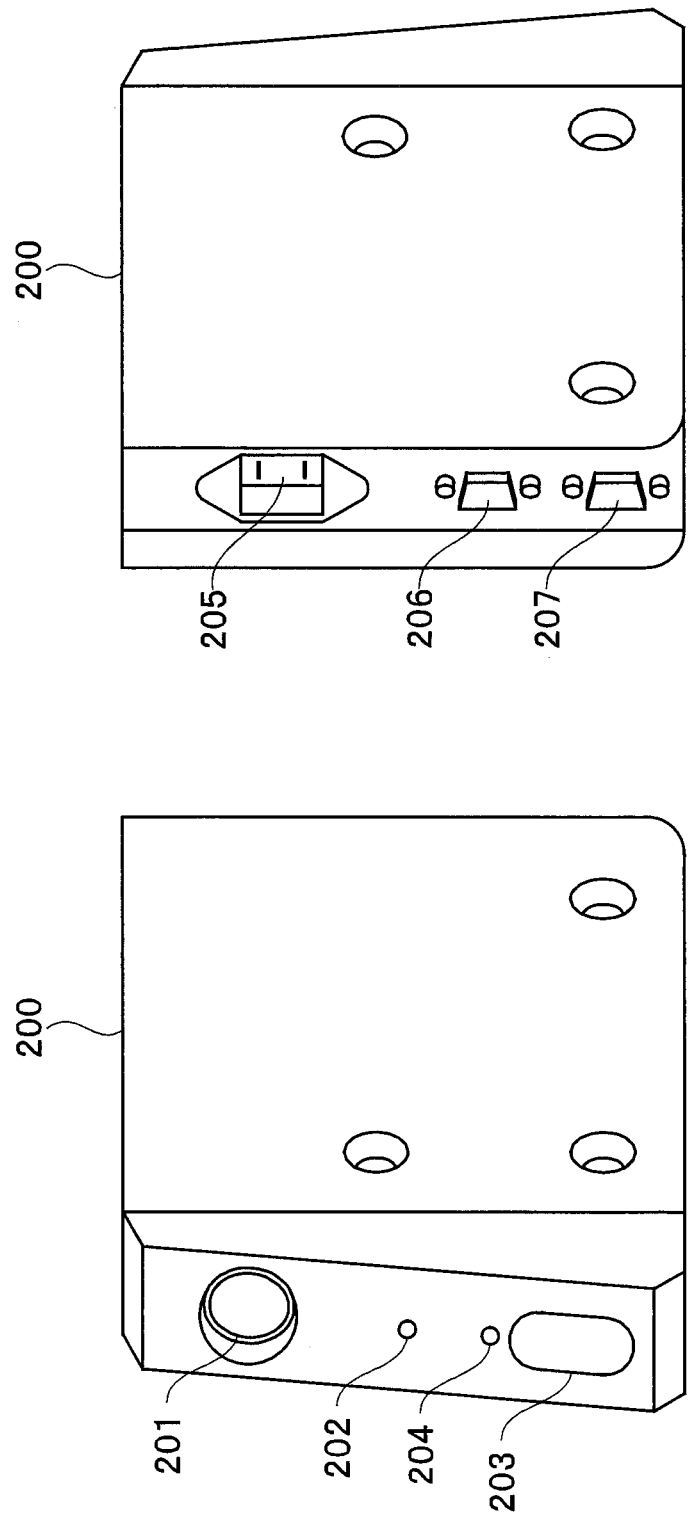

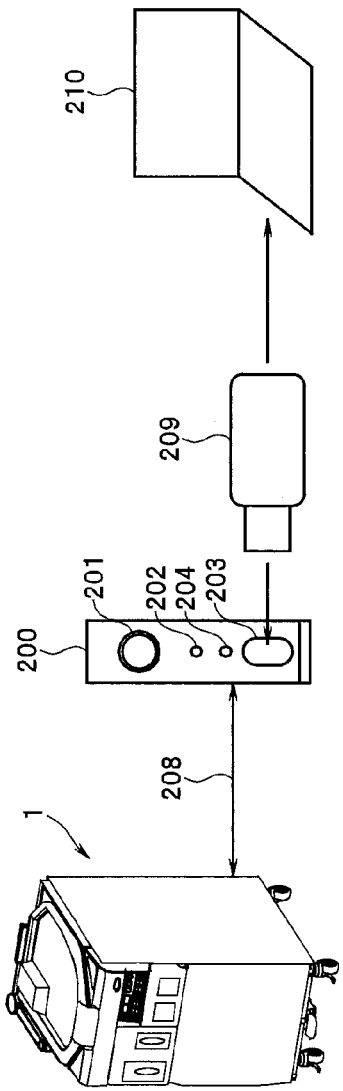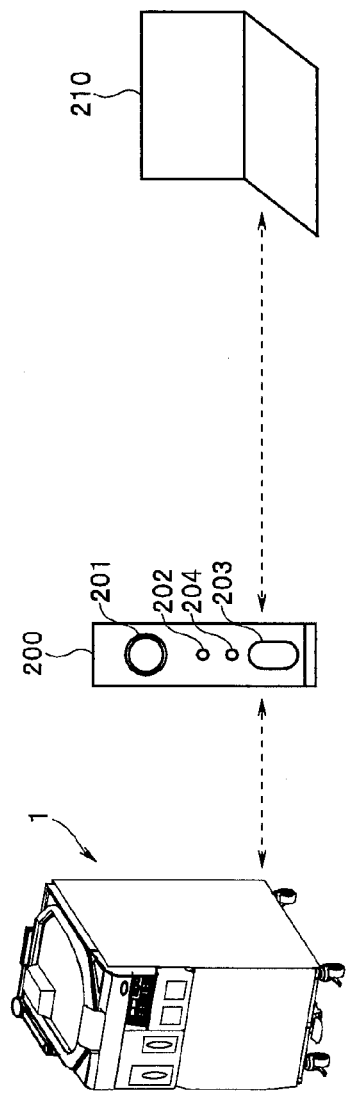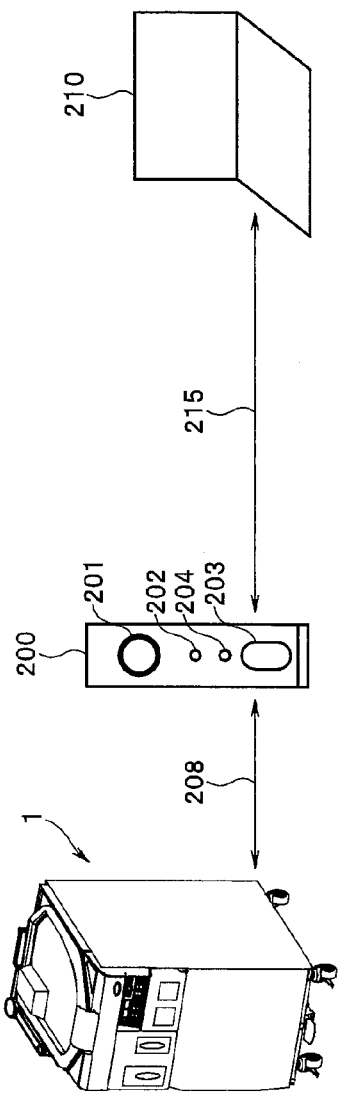
FIG.29A
FIG.29B
FIG.29C

CLEANING/DISINFECTING APPARATUS

CROSS REFERENCE TO RELATED APPLICATION

This application is a continuation application of PCT/JP2013/065340 filed on Jun. 3, 2013 and claims benefit of Japanese Application No. 2012-191181 filed in Japan on Aug. 31, 2012, the entire contents of which are incorporated herein by this reference.

BACKGROUND OF THE INVENTION

1. Field of the Invention

The present invention relates to a cleaning/disinfecting apparatus, and specifically relates to a cleaning/disinfecting apparatus that can execute a plurality of cleaning/disinfection menus simultaneously.

2. Description of the Related Art

Conventionally, in an endoscope used for examination and treatment of the inside of a body, filth adheres not only to an outer surface of an insertion portion inserted into the body, but also to respective endoscope conduits such as an air/water feeding conduit, a suction conduit and a treatment instrument insertion conduit. Therefore, it is necessary to clean and disinfect not only the outer surface of the endoscope but also the insides of the respective endoscope conduits without fail. Examples of such conventional endoscope cleaning/disinfecting apparatuses for cleaning and disinfecting an endoscope includes an endoscope cleaning/disinfecting apparatus indicated in Japanese Patent Application Laid-Open Publication No. 11-276434.

The endoscope cleaning/disinfecting apparatus in Japanese Patent Application Laid-Open Publication No. 11-276434 includes a cleaning bath and can clean and disinfect an endoscope after the end of an examination by setting the endoscope in the cleaning bath. More specifically, an endoscope after use is set in the cleaning bath, and upon operation of various operation switches, respective steps of cleaning, disinfection, rinsing and air feeding are automatically performed based on instructions from a control portion.

As disclosed in Japanese Patent Application Laid-Open Publication No. 11-276434, in a conventional cleaning/disinfecting apparatus, only one attachment portion to which an endoscope is to be attached is provided, and a cleaning/disinfection menu is executed for only one endoscope. For work efficiency enhancement, it is preferable to execute a cleaning/disinfection menu for a plurality of endoscopes simultaneously. Thus, a plurality of attachment portions may be provided in a conventional cleaning/disinfecting apparatus so that a plurality of endoscopes can be attached to the attachment portions.

SUMMARY OF THE INVENTION

A cleaning/disinfecting apparatus according to an aspect of the present invention includes: a plurality of attachment portions for attaching an endoscope; a cleaning/disinfecting portion that communicates with the plurality of attachment portions, and can execute different types of cleaning/disinfection menus for the respective attachment portions simultaneously; an endoscope information reading portion that reads endoscope information from the endoscope; a control portion that determines a cleaning/disinfection menu from among the cleaning/disinfection menus based on the endoscope information, and outputs attachment portion identifying information for identifying an attachment portion for executing the determined cleaning/disinfection menu; and a notifying portion that notifies the attachment portion identifying information outputted from the control portion.

BRIEF DESCRIPTION OF THE DRAWINGS

FIG. 4 is a diagram for illustrating an example of a table stored in a storage portion in a cleaning/disinfecting apparatus 1;

FIG. 5 is a diagram showing example display of connection information displayed on a notifying portion 7;

FIG. 6 is a diagram for illustrating an example of a case where two cleaning/disinfection menus are executed simultaneously;

FIG. 7 is a diagram for illustrating a cleaning/disinfecting tube to be connected to an endoscope 100a;

FIG. 19 is a diagram showing a configuration of a cleaning/disinfecting apparatus according to a seventh embodiment;

FIG. 28A is a perspective diagram of a history management unit as obliquely viewed from the front;

FIG. 28B is a perspective diagram of the history management unit as obliquely viewed from the back;

FIG. 29A is a diagram for illustrating data communications via a history management unit 200;

FIG. 29B is a diagram for illustrating data communications via a history management unit 200;

FIG. 29C is a diagram for illustrating data communications via a history management unit 200;

DETAILED DESCRIPTION OF THE PREFERRED EMBODIMENT(S)

Embodiments of the present invention will now be described with reference to the drawings.
(First Embodiment)

Figure 1:
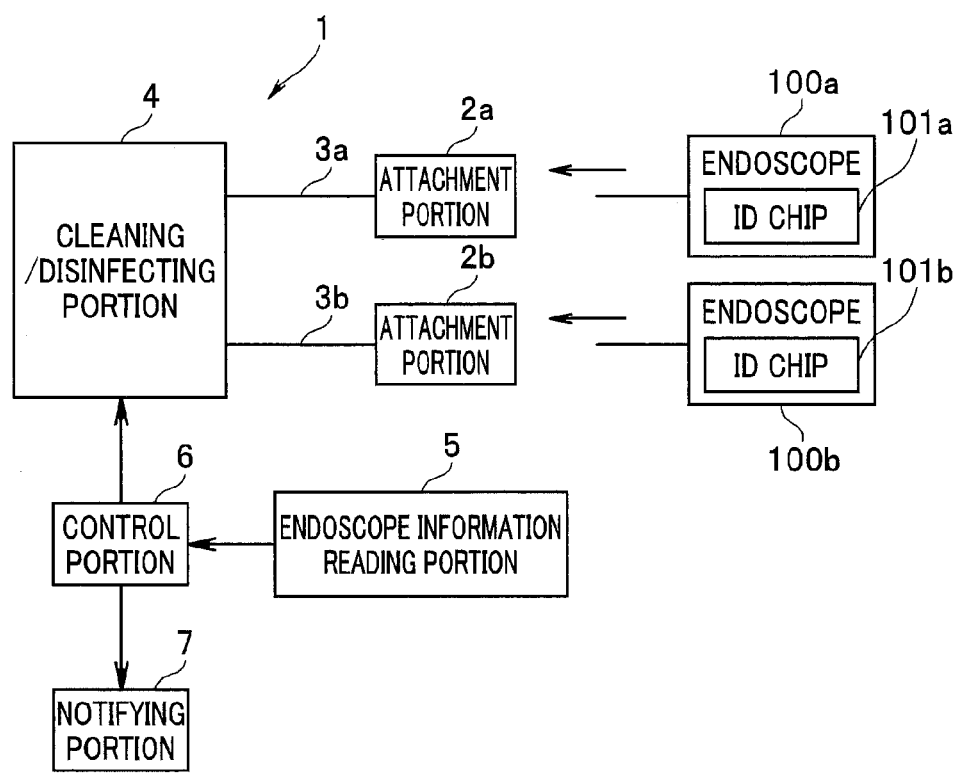
FIG. 1 is a diagram showing a configuration of a cleaning/disinfecting apparatus according to a first embodiment.

FIG. 1 is a diagram showing a configuration of a cleaning/disinfecting apparatus according to a first embodiment.

As shown in FIG. 1, a cleaning/disinfecting apparatus 1 includes a plurality of attachment portions (2a and 2b), a plurality of conduits (3a and 3b), a cleaning/disinfecting portion 4, an endoscope information reading portion 5, a control portion 6, and a notifying portion 7. Although the cleaning/disinfecting apparatus 1 includes the two attachment portions 2a and 2b and the two conduits 3a and 3b in FIG. 1, the numbers of attachment portions and conduits may also be three or more.

Endoscopes 100a and 100b are attached to the attachment portions 2a and 2b. Types of the endoscopes 100a and 100b may be different. An endoscope may be attached to each attachment portion directly or via a tubular cleaning tube.

In the endoscope 100a, an ID chip 101a on which endoscope information of the endoscope 100a is recorded is incorporated. Similarly, in the endoscope 100b, an ID chip 101b on which endoscope information of the endoscope 100b is recorded is incorporated. It should be noted that the ID chips 101a and 101b may also be integrally provided on outsides of the endoscopes 100a and 100b, respectively so as not to come off the endoscopes 100a and 100b.

Examples of the endoscope information include, e.g., endoscope type, serial number, conduit lengths, conduit diameters, internal space volume, use history, last-employed procedure and time period elapsed after use.

The attachment portion 2a is connected to a distal end of the conduit 3a, and the cleaning/disinfecting portion 4 is connected to a rear end. The conduit 3a communicates via the attachment portion 2a with an inside of the endoscope 100a attached to the attachment portion 2a. Similarly, the attachment portion 2b is connected to a distal end of the conduit 3b, and the cleaning/disinfecting portion 4 is connected to a rear end. The conduit 3b communicates via the attachment portion 2b with an inside of the second endoscope 100b attached to the attachment portion 2b.

The cleaning/disinfecting portion 4 communicates with the attachment portions 2a and 2b via the conduits 3a and 3b, respectively. Also, the cleaning/disinfecting portion 4 can simultaneously execute different types of cleaning/disinfection menus for the respective attachment portions 2a and 2b to which the endoscopes 100a and 100b are attached, based on the control by the control portion 6. Details of the cleaning/disinfecting portion 4 will be described later.

A cleaning/disinfection menu refers to settings for cleaning or disinfecting an endoscope, and includes at least one step from a group consisting of, for example, cleaning, rinsing, disinfection, air feeding and alcohol flush. A cleaning/disinfection menu can be varied by, e.g., selecting which steps to include, changing lengths of the respective steps, changing temperatures in the respective steps, changing a composition of a chemical or changing a concentration of the chemical.

For example, where endoscopes with different channel lengths are cleaned simultaneously, a cleaning/disinfection menu can be varied by increasing a cleaning time period, increasing a temperature of a chemical or increasing a concentration of the chemical for an endoscope with a longer channel compared to that of an endoscope with a shorter channel.

For example, where endoscopes with different time periods elapsed after use are cleaned simultaneously, a cleaning/disinfection menu can be varied by increasing a cleaning time period, increasing a temperature of a chemical or increasing a concentration of the chemical for an endoscope with a longer time period elapsed after use compared to that of an endoscope with a shorter time period elapsed after use.

The endoscope information reading portion 5 is, for example, an RFID antenna. The endoscope information reading portion 5 reads out endoscope information on the endoscope 100a from the ID chip 101a and outputs the read-out endoscope information on the endoscope 100a to the control portion 6. Similarly, the endoscope information reading portion 5 reads out endoscope information on the endoscope 100b from the ID chip 101b and outputs the read-out endoscope information on the endoscope 100b to the control portion 6. To adapt the endoscope information reading portion 5 to an endoscope without an ID chip, the portion 5 may have a function to read out endoscope information by a conventionally known method other than an RFID, or a user may also input endoscope information manually or by bar code.

The control portion 6 determines a cleaning/disinfection menu for the endoscope 100a based on the inputted endoscope information on the endoscope 100a and assigns the determined cleaning/disinfection menu to any one of the attachment portions 2a and 2b for which the menu is executed. It should be noted that in the following description, it is assumed that a cleaning/disinfection menu of the endoscope 100a is assigned to the attachment portion 2a. The control portion 6 outputs to the notifying portion 7 attachment portion identifying information for identifying the assigned attachment portion 2a.

The notifying portion 7 notifies attachment portion identifying information for identifying the assigned attachment portion 2a inputted from the control portion 6. A checker attaches the endoscope 100a to be cleaned and disinfected to the attachment portion 2a based on the attachment portion identifying information which has been notified.

Next, the control portion 6 determines a cleaning/disinfection menu for the endoscope 100b based on the inputted endoscope information on the endoscope 100b and assigns the determined cleaning/disinfection menu to any one of the attachment portions 2a and 2b for which the menu is executed. It should be noted that in the following description, it is assumed that a cleaning/disinfection menu of the endoscope 100b is assigned to the attachment portion 2b. The control portion 6 outputs to the notifying portion 7 attachment portion identifying information for identifying the assigned attachment portion 2b.

The notifying portion 7 notifies the attachment portion identifying information, inputted from the control portion 6, for identifying the assigned attachment portion 2b. A checker attaches the endoscope 100b to be cleaned and disinfected to the attachment portion 2b based on the provided attachment portion identifying information.

The notifying portion 7 is, for example, a display that displays a name or a position of the assigned attachment portion 2a or 2b. It should be noted that the notifying portion 7 may also be a lighting portion such as an LED installed in each of the attachment portions 2a and 2b, or installed near each of the attachment portions 2a and 2b. In such a case, only a lighting portion installed in or near the assigned attachment portion 2a or 2b illuminates or blinks. Alternatively, a color of a lighting portion may be changed based on the attachment portion identifying information.

Also, the notifying portion 7 may be a voice outputting portion such as a speaker that outputs a name or a position of the assigned attachment portion 2a or 2b by voice.

Next, an operation of the cleaning/disinfecting apparatus 1 having such a configuration will be described.

First, the checker turns on a power supply, not shown, of the cleaning/disinfecting apparatus 1 to cause the endoscope information reading portion 5 to read the endoscope information recorded on the ID chip 101a of the endoscope 100a for which a cleaning/disinfection menu is executed. The endoscope information on the endoscope 100a read by the endoscope information reading portion 5 is supplied to the control portion 6.

Based on the supplied endoscope information, the control portion 6 determines a cleaning/disinfection menu for the endoscope 100a and assigns the cleaning/disinfection menu for the endoscope 100a to the attachment portion 2a. Then, attachment portion identifying information for identifying the assigned attachment portion 2a is outputted from the control portion 6 to the notifying portion 7, and the notifying portion 7 notifies the attachment portion identifying information. As a result, the checker is allowed to attach the endoscope 100a to the attachment portion 2a to which the cleaning/disinfection menu for the endoscope 100a is assigned.

Next, the checker causes the endoscope information reading portion 5 to read endoscope information recorded on the ID chip 101b of the endoscope 100b for which a cleaning/ disinfection menu is executed. The endoscope information on the endoscope 100b read by the endoscope information reading portion 5 is supplied to the control portion 6.

Based on the supplied endoscope information, the control portion 6 determines a cleaning/disinfection menu for the endoscope 100b and assigns the cleaning/disinfection menu for the endoscope 100b to the attachment portion 2b. Then, attachment portion identifying information for identifying the assigned attachment portion 2b is outputted from the control portion 6 to the notifying portion 7, and the notifying portion 7 notifies the attachment portion identifying information. As a result, the checker is allowed to attach the endoscope 100b to the attachment portion 2b to which the cleaning/disinfection menu for the endoscope 100b is assigned.

Thus, in the cleaning/disinfecting apparatus 1, the endoscope information reading portion 5 reads endoscope information on an endoscope for which a cleaning/disinfection menu is executed, for example, the endoscope 100a, and assigns the cleaning/disinfection menu to one of the attachment portions 2a and 2b, for example, the attachment portion 2a. Then, the cleaning/disinfecting apparatus 1 causes the notifying portion 7 to notify attachment portion identifying information for identifying the attachment portion 2a to which the cleaning/disinfection menu is assigned. Similarly, for the endoscope 100b, the cleaning/disinfecting apparatus 1 causes the notifying portion 7 to notify attachment portion identifying information for identifying the attachment portion 2b to which a cleaning/disinfection menu is assigned. As a result, the checker is allowed to easily recognize the attachment portions 2a and 2b to which the endoscopes 100a and 100b are to be attached.

Therefore, according to the cleaning/disinfecting apparatus of the present embodiment, when cleaning/disinfection menus are executed for a plurality of endoscopes, erroneous connection can be prevented.

(Second Embodiment)

Next, a second embodiment will be described.

Before a checker executes cleaning/disinfection menus using the cleaning/disinfecting apparatus 1, the checker needs to check if no holes or the like causing air leakage are formed inside the endoscopes 100a and 100b. Therefore, the cleaning/disinfecting apparatus 1 includes a water leakage sensing portion for conducting a water leakage check to check if no water leakage sites such as holes causing air leakage are formed. The present embodiment will be described in terms of a cleaning/disinfecting apparatus including a water leakage sensing portion that can prevent misconnection when a water leakage check is conducted for a plurality of endoscopes.

Figure 2:
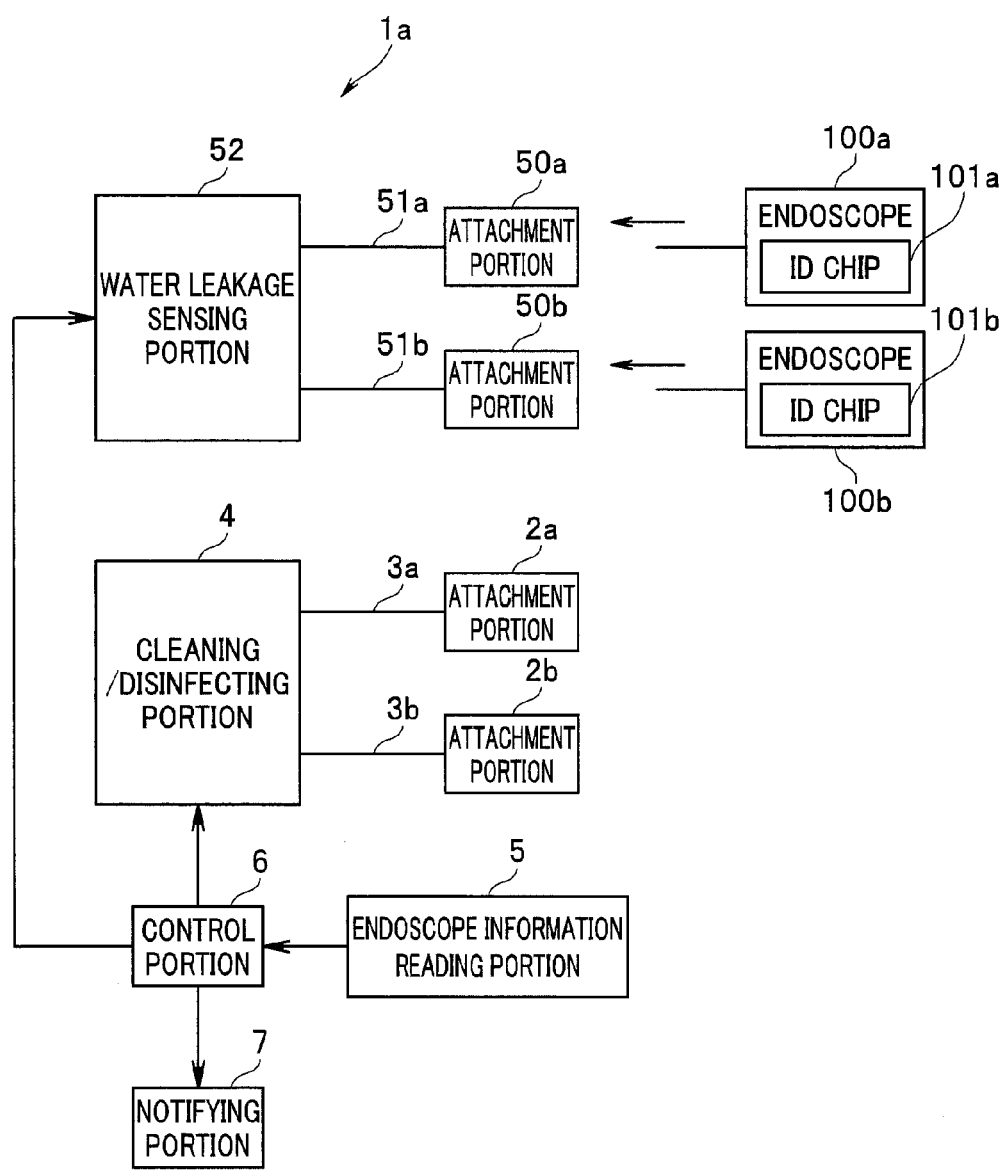
FIG. 2 is a diagram showing a configuration of a cleaning/disinfecting apparatus according to a second embodiment.

FIG. 2 is a diagram showing a configuration of a cleaning/ disinfecting apparatus according to a second embodiment. In FIG. 2, components similar to those in FIG. 1 are provided with reference numerals that are the same as those in FIG. 1, and a description thereof will be omitted.

As illustrated in FIG. 2, a cleaning/disinfecting apparatus 1a is configured by adding a plurality of, here, two attachment portions 50a and 50b, a plurality of, here, two conduits 51a and 51b, and a water leakage sensing portion 52 to the cleaning/disinfecting apparatus 1 in FIG. 1. Although the cleaning/ disinfecting apparatus 1a has a configuration including two attachment portions 50a and 50b and two conduits 51a and 51b, the cleaning/disinfecting apparatus 1a may have a configuration including three or more attachment portions and three or more conduits.

The attachment portion 50a is connected to a distal end of the conduit 51a, and the water leakage sensing portion 52 is connected to a rear end of the conduit 51a. The conduit 51a communicates with the inside of an endoscope 100a attached to the attachment portion 50a, via the attachment portion 50a. Likewise, the attachment portion 50b is connected to a distal end of the conduit 51b, and the water leakage sensing portion 52 is connected to a rear end of the conduit 51b. The conduit 51b communicates with the inside of a second endoscope 100b attached to the attachment portion 50b, via the attachment portion 50b.

The water leakage sensing portion 52 communicates with the attachment portions 50a and 50b via the conduits 51a and 51b, respectively. Also, the water leakage sensing portion 52 can execute a plurality of water leakage check menus simultaneously for the endoscopes 100*a* and 100*b* attached to the attachment portions 50*a* and 50*b*, based on control by a control portion 6.

An endoscope information reading portion 5 reads endoscope information on the endoscope 100*a* from an ID chip 101*a*, and outputs the read endoscope information on the endoscope 100*a* to the control portion 6. Likewise, the endoscope information reading portion 5 reads endoscope information on the endoscope 100*b* from an ID chip 101*b*, and outputs the read endoscope information on the endoscope 100*b* to the control portion 6.

The control portion 6 determines a water leakage check menu for the endoscope 100*a* based on the input endoscope information on the endoscope 100*a*, and assigns the determined water leakage check menu to either of the attachment portions 50*a* and 50*b* to execute the water leakage check menu. The below description will be provided assuming that the water leakage check menu for the endoscope 100*a* is assigned to the attachment portion 50*a*. The control portion 6 outputs attachment portion identifying information for identifying the assigned attachment portion 50*a*, to a notifying portion 7.

The notifying portion 7 provides a notification of attachment portion identifying information for identifying the assigned attachment portion 50*a*, which has been inputted from the control portion 6. A checker attaches the endoscope 100*a* for water leakage sensing to the attachment portion 50*a* based on the provided attachment portion identifying information.

Next, the control portion 6 determines a water leakage check menu for the endoscope 100*b* based on the input endoscope information on the endoscope 100*b*, and assigns the determined water leakage check menu to either of the attachment portions 50*a* and 50*b* to execute the water leakage check menu. The below description will be provided assuming that the water leakage check menu for the endoscope 100*b* is assigned to the attachment portion 50*b*. The control portion 6 outputs attachment portion identifying information for identifying the assigned attachment portion 50*b*, to the notifying portion 7.

The notifying portion 7 provides a notification of the attachment portion identifying information for identifying the assigned attachment portion 50*b*, which has been inputted from the control portion 6. The checker attaches the endoscope 100*b* for water leakage sensing to the attachment portion 50*b* based on the provided attachment portion identifying information.

Next, an operation of the cleaning/disinfecting apparatus 12 configured as described above will be described.

First, a checker turns on a non-illustrated power supply in the cleaning/disinfecting apparatus 1*a* and makes the endoscope information reading portion 5 read the endoscope information recorded in the ID chip 101*a* in the endoscope 100*a* for which a water leakage check is conducted. The endoscope information on the endoscope 100*a*, which has been read by the endoscope information reading portion 5, is supplied to the control portion 6.

A water leakage check menu for the endoscope 100*a* is determined by the control portion 6 based on the supplied endoscope information, and the water leakage check menu for the endoscope 100*a* is assigned to the attachment portion 50*a*. Then, the attachment portion identifying information for identifying the assigned attachment portion 50*a* is outputted from the control portion 6 to the notifying portion 7, and a notification of the attachment portion identifying information is provided by the notifying portion 7. As a result, the checker can attach the endoscope 100*a* to the attachment portion 50*a* assigned with the water leakage check menu for the endoscope 100*a*.

Next, the checker makes endoscope information reading portion 5 read the endoscope information recorded in the ID chip 101*b* in the endoscope 100*b* for which a water leakage check is conducted. The endoscope information on the endoscope 100*b*, which has been read by the endoscope information reading portion 5, is supplied to the control portion 6.

A water leakage check menu for the endoscope 100*b* is determined by the control portion 6 based on the supplied endoscope information, and the water leakage check menu for the endoscope 100*b* is assigned to the attachment portion 50*b*. Then, attachment portion identifying information for identifying the assigned attachment portion 50*b* is outputted from the control portion 6 to the notifying portion 7, and a notification of the attachment portion identifying information is provided by the notifying portion 7. As a result, the checker can attach the endoscope 100*b* to the attachment portion 50*b* assigned with the water leakage check menu for the endoscope 100*b*.

As described above, the cleaning/disinfecting apparatus 1*a* reads endoscope information on an endoscope for which a water leakage check is to be conducted, for example, an endoscope 100*a*, via the endoscope information reading portion 5, and assigns a water leakage check menu to one attachment portion from among the plurality of attachment portions 50*a* and 50*b*, for example, the attachment portion 50*a*. Then, the cleaning/disinfecting apparatus 1*a* provides a notification of attachment portion identifying information for identifying the attachment portion 50*a* assigned with the water leakage check menu, via the notifying portion 7. Also, the cleaning/disinfecting apparatus 1*a* provides a notification of attachment portion identifying information for identifying the attachment portion 50*b* assigned with a water leakage check menu for the endoscope 100*b*, via the notifying portion 7 in a manner similar to the above. As a result, the checker can easily recognize the attachment portions 50*a* and 50*b* to which the plurality of endoscopes 100*a* and 100*b* are to be attached.

Accordingly, the cleaning/disinfecting apparatus according to the present embodiment enables prevention of misconnection when a water leakage check is conducted for a plurality of endoscopes.

(Third Embodiment)

Next, a third embodiment will be described. Although a cleaning/disinfecting apparatus and an endoscope can directly be connected, it is generally necessary to connect a cleaning/disinfecting apparatus and an endoscope via a cleaning/disinfecting tube. The cleaning/disinfecting tube varies depending on the endoscope, and one connection part or a plurality of connection parts are provided on the cleaning/disinfecting apparatus side, making a method for connection of the cleaning/disinfecting tube be complicated. Furthermore, a checker does not know tube information that varies depending on the endoscope and thus, cannot perform connection of a cleaning/disinfecting tube unless the checker looks into an instruction manual or the like. Therefore, the present embodiment will be described in terms of a cleaning/disinfecting apparatus that facilitates cleaning/disinfecting tube connection. A cleaning/disinfecting apparatus according to the present embodiment has a configuration that is similar to those of the cleaning/disinfecting apparatuses in FIGS. 1 and 2.

Figure 3:
FIG. 3 is a diagram for illustrating an example of a table stored in an ID chip.

A table 60, which is illustrated in FIG. 3, is stored in each of an ID chip 101*a* in an endoscope 100*a* and an ID chip 101*b* in an endoscope 100b. FIG. 3 is a diagram for illustrating an example of a table stored in an ID chip.

The table 60 illustrated in FIG. 3 includes names of cleaning/disinfecting tubes to be connected to the endoscope 100a and the endoscope 100b and indices relating to parts to which the respective cleaning/disinfecting tubes are to be connected. Since two cleaning/disinfecting tubes may be provided for biopsy, one for suction, one for air/water feeding, one for a jet conduit and one for a forceps elevator, a maximum of six cleaning/disinfecting tubes may be provided. The information on the table 60 is read by an endoscope information reading portion 5 in the cleaning/disinfecting apparatus 1 and outputted to a control portion 6.

Upon receipt of the information on the table 60 from the ID chip 101a in the first endoscope 100a, the control portion 6 refers to a table 61 stored in a non-illustrated storage portion, which is illustrated in FIG. 4. FIG. 4 is a diagram for illustrating an example of the table stored in the storage portion in the cleaning/disinfecting apparatus 1.

The table 61 illustrated in FIG. 4 is a table for designating a type of each cleaning/disinfecting tube according to an index of the cleaning/disinfecting tube. The control portion 6 determines a connector to be connected, here, an attachment portion 2a or 2b according to a type of a cleaning/disinfecting tube in the table 61. The control portion 6 makes the determined connection part to which the cleaning/disinfecting tube is to be connected and tube information on the cleaning/disinfecting tube be displayed on the notifying portion 7.

FIG. 5 is a diagram showing example display of connection information displayed on the notifying portion 7.

The attachment portions 2a and 2b for cleaning/disinfection in the cleaning/disinfecting apparatus 1 are assigned with, for example, white, and provided with names, white 1 and white 2, respectively, as attachment portion names Also, the cleaning/disinfecting apparatus 1 includes, for example, attachment portions assigned with violet, violet 1 and violet 2, attachment portions assigned with light blue, light blue 1 and light blue 2, and attachment portions assigned with green, green 1 and green 2, as non-illustrated attachment portions for cleaning and disinfection. Furthermore, attachment portions 50a and 50b for water leakage sensing in the cleaning/disinfecting apparatus 1 are assigned with, for example, black, and provided with names, black 1 and black 2, respectively, as attachment portion names.

A checker confirms names of cleaning/disinfecting tubes to be connected and parts to which the cleaning/disinfecting tubes are to be connected based on the connection information in FIG. 5 displayed on the notifying portion 7, and connects the first endoscope 100a to the cleaning/disinfecting apparatus 1. The checker also performs processing similar to the above for a second endoscope 100b to connect the endoscope 100b to the cleaning/disinfecting apparatus 1. Here, if the control portion 6 determines that there are not sufficient attachment portions to be connected to the second endoscopes 100b, for example, display of "two endoscopes cannot be processed simultaneously" is provided on the notifying portion 7. In this case, the checker executes a cleaning/disinfection menu only for the first endoscope 100a. If the second endoscope 100b can also be connected to the cleaning/disinfecting apparatus 1, the checker executes cleaning/disinfection menus for the two endoscopes simultaneously.

Here, processing for executing cleaning/disinfection menus for two endoscopes simultaneously will be described.

FIG. 6 is a diagram for illustrating an example of a case where cleaning/disinfection menus are executed for two endoscopes simultaneously.

Cleaning/disinfection menus for endoscopes vary depending on the number, the lengths and the diameters of conduits and the capacity of the respective endoscopes. In the present embodiment, it is assumed that the endoscope 100a includes long conduits and has a large capacity. Meanwhile, it is assumed that the endoscope 100b has short conduits and has a small capacity. Endoscopes are classified into not only these two categories, but also into finer categories according to the number, the lengths and the diameters of conduits and the capacity of the endoscope.

First, before cleaning/disinfection menus are executed, a water leakage check, which has been described in the second embodiment, is conducted. Subsequently, if there is no water leakage in the endoscopes 100a and 100b, the cleaning/disinfection menus are executed. In each of the cleaning/disinfection menus, the processing is performed in the order of cleaning, rinsing, disinfection, rinsing, air feeding and alcohol flush.

For the endoscope 100a having long conduits and a large capacity, a program for large capacity is executed in a water leakage check, and a cleaning/disinfection menu with a long cleaning time period, a long rising time period, a normal disinfection time period, a long cleaning time period, a long air feeding time period and a large amount of alcohol flush is executed. On the other hand, for endoscope 100b having short conduits and a small capacity, a program for small capacity is performed in a water leakage check, and a cleaning/disinfection menu with a short cleaning time period, a short rising time period, a normal disinfection time period, a short cleaning time period, a short air feeding time period and a small amount of alcohol flush is executed.

Where cleaning/disinfection menus for the endoscopes 100a and 100b are simultaneously executed, individual cleaning/disinfection menus may be executed; however, it is also possible to employ conditions such as the cleaning time period and the rising time period before disinfection and the rising time period and the air feeding time period after disinfection in the processing for the endoscopes with long conduits, for the endoscope with the short conduits.

Next, cleaning/disinfecting tubes to be connected between the cleaning/disinfecting apparatus 1 and the endoscopes 100a and 100b and examples in which the endoscopes 100a and 100b are set in the cleaning/disinfecting apparatus 1 will be described.

Figure 7:
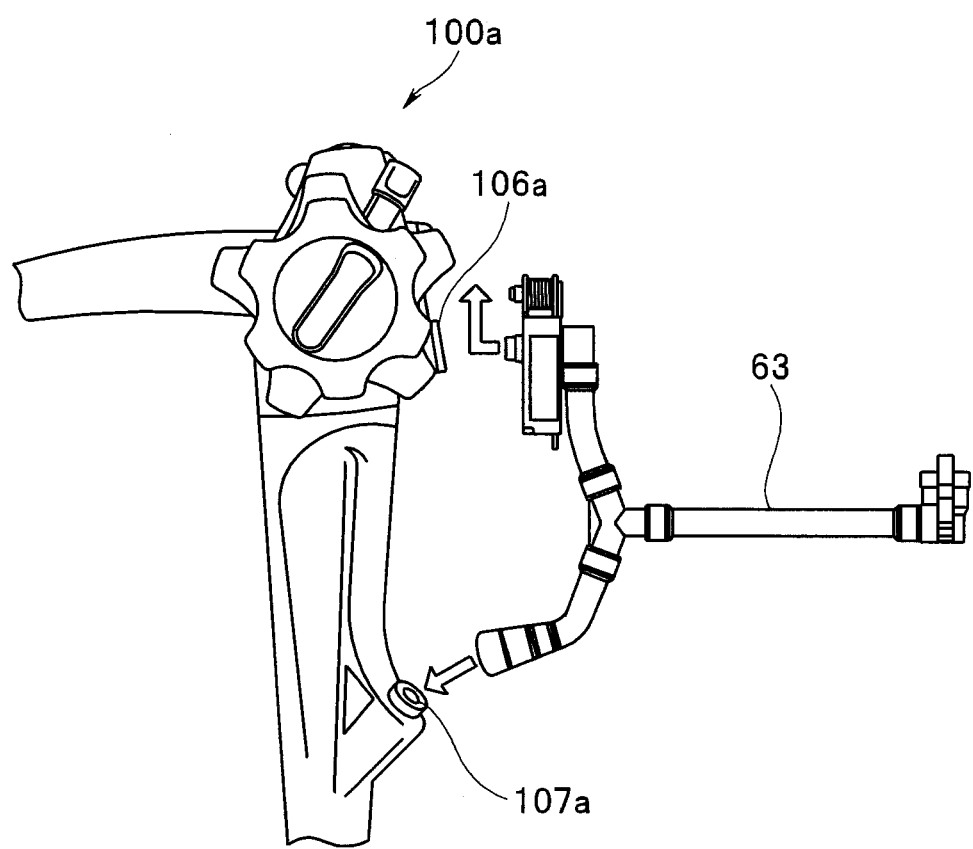
Figure 8:
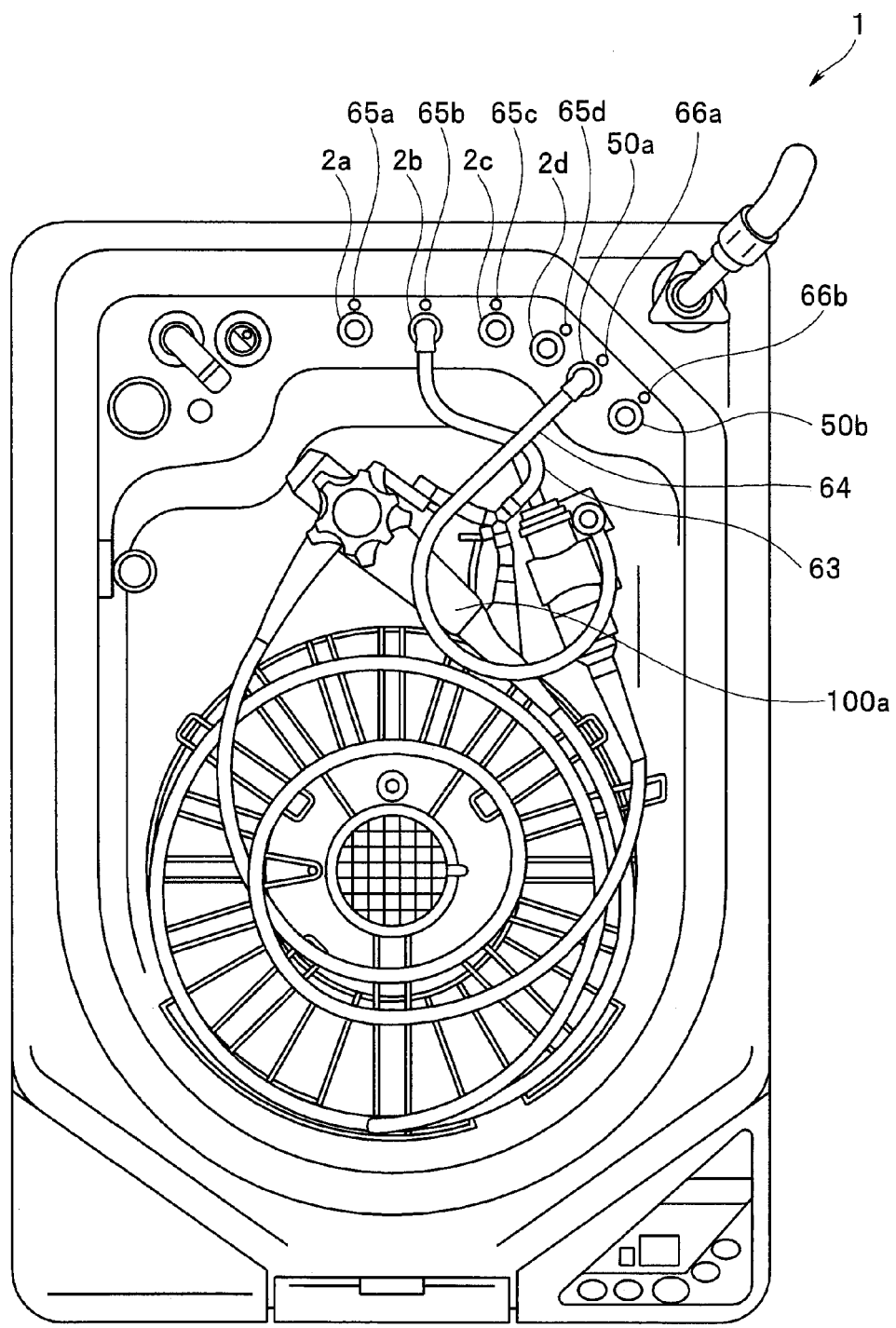
FIG. 8 is a diagram for illustrating an example in which the endoscope 100a is set in the cleaning/disinfecting apparatus 1.

FIG. 7 is a diagram for illustrating a cleaning/disinfecting tube to be connected to the endoscope 100a, and FIG. 8 is a diagram for illustrating an example in which the endoscope 100a is set in the cleaning/disinfecting apparatus 1.

As illustrated in FIG. 7, ends on one side of a cleaning/disinfecting tube 63 to be connected to the endoscope 100a are connected to a sleeve 106a for a suction conduit and a sleeve 107a for a forceps port in the endoscope 100a. On the other hand, as illustrated in FIG. 8, an end on the other side of the cleaning/disinfecting tube 63 is connected to the attachment portion 2b in the cleaning/disinfecting apparatus 1. Also, an end of a water leakage sensing tube 64 is connected to the endoscope 100a, and the other end of the water leakage sensing tube 64 is connected to the attachment portion 50a. A checker connects the cleaning/disinfecting tube 63 to the cleaning/disinfecting apparatus 1 as in FIG. 8, based on connection information displayed on the notifying portion 7.

LEDs 65a to 65d are arranged adjacent to attachment portions 2a to 2d for cleaning/disinfection, respectively. Also, LEDs 66a and 66b are arranged adjacent to the attachment portions 50a and 50b for water leakage sensing, respectively. Notification of connection information is not limited to display of connection information in FIG. 5 by the notifying portion 7, but may be provided by lighting or blinking the LEDs 65a to 65d and LEDs 66a and 66b to provide notification of attachment portions 2a to 2d and 50a and 50b to which the cleaning/disinfecting tube 63 and the water leakage sensing tube 64 are to be connected.

Figure 9:
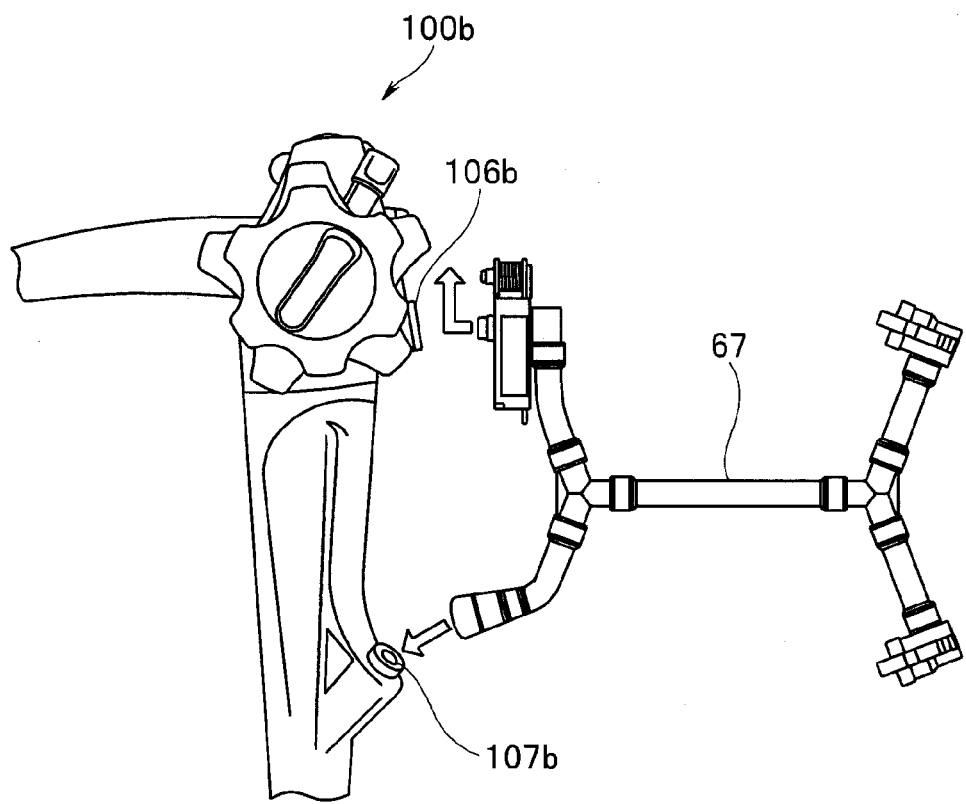
FIG. 9 is a diagram for illustrating a cleaning/disinfecting tube to be connected to an endoscope 100b.
Figure 10:
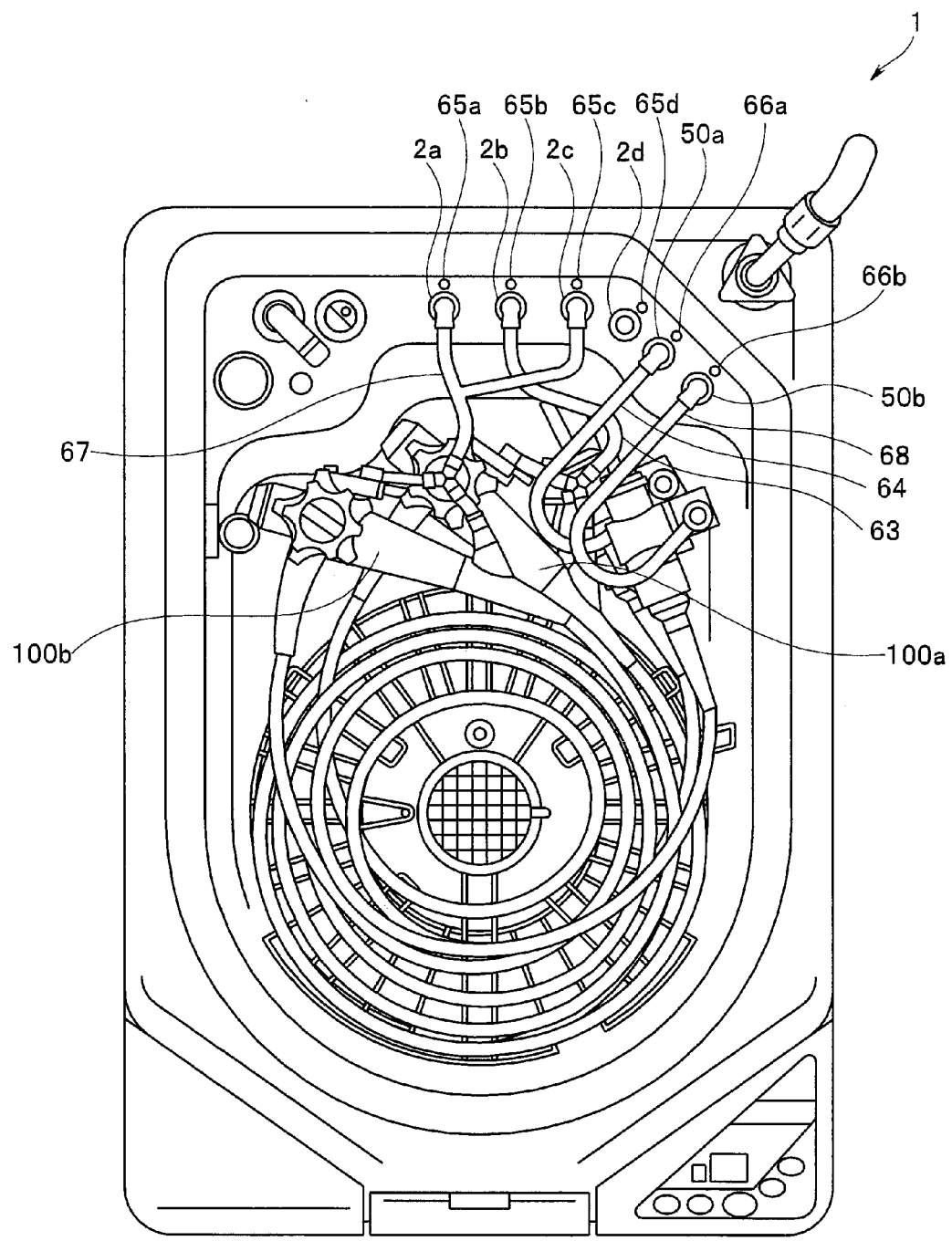
FIG. 10 is a diagram for illustrating an example in which the endoscopes 100a and 100b are set in the cleaning/disinfecting apparatus 1.

FIG. 9 is a diagram for illustrating a cleaning/disinfecting tube to be connected to the endoscope 100b, and FIG. 10 is a diagram for illustrating an example in which the endoscopes 100a and 100b are set in the cleaning/disinfecting apparatus 1.

As illustrated in FIG. 9, ends on one side of a cleaning/disinfecting tube 67 to be connected to the endoscope 100b are connected to a sleeve 106b for a suction conduit and a sleeve 107b for a forceps port in the endoscope 100b. On the other hand, an end on the other side of the cleaning/disinfecting tube 67 is biforked and connected to attachment portions 2a and 2c in the cleaning/disinfecting apparatus 1 as illustrated in FIG. 10. Also, an end of a water leakage sensing tube 68 is connected to the endoscope 100b, and the other end of the water leakage sensing tube 68 is connected to the attachment portion 50b for water leakage sensing. The checker connects the cleaning/disinfecting tube 67 to the cleaning/disinfecting apparatus 1 as illustrated in FIG. 10, based on the connection information displayed on the notifying portion 7, enabling the endoscopes 100a and 100b to be set in the cleaning/disinfecting apparatus 1 without the respective tubes being connected to wrong attachment portions 2a to 2d.

Next, cleaning/disinfecting tube connection processing will be described.

Figure 11:
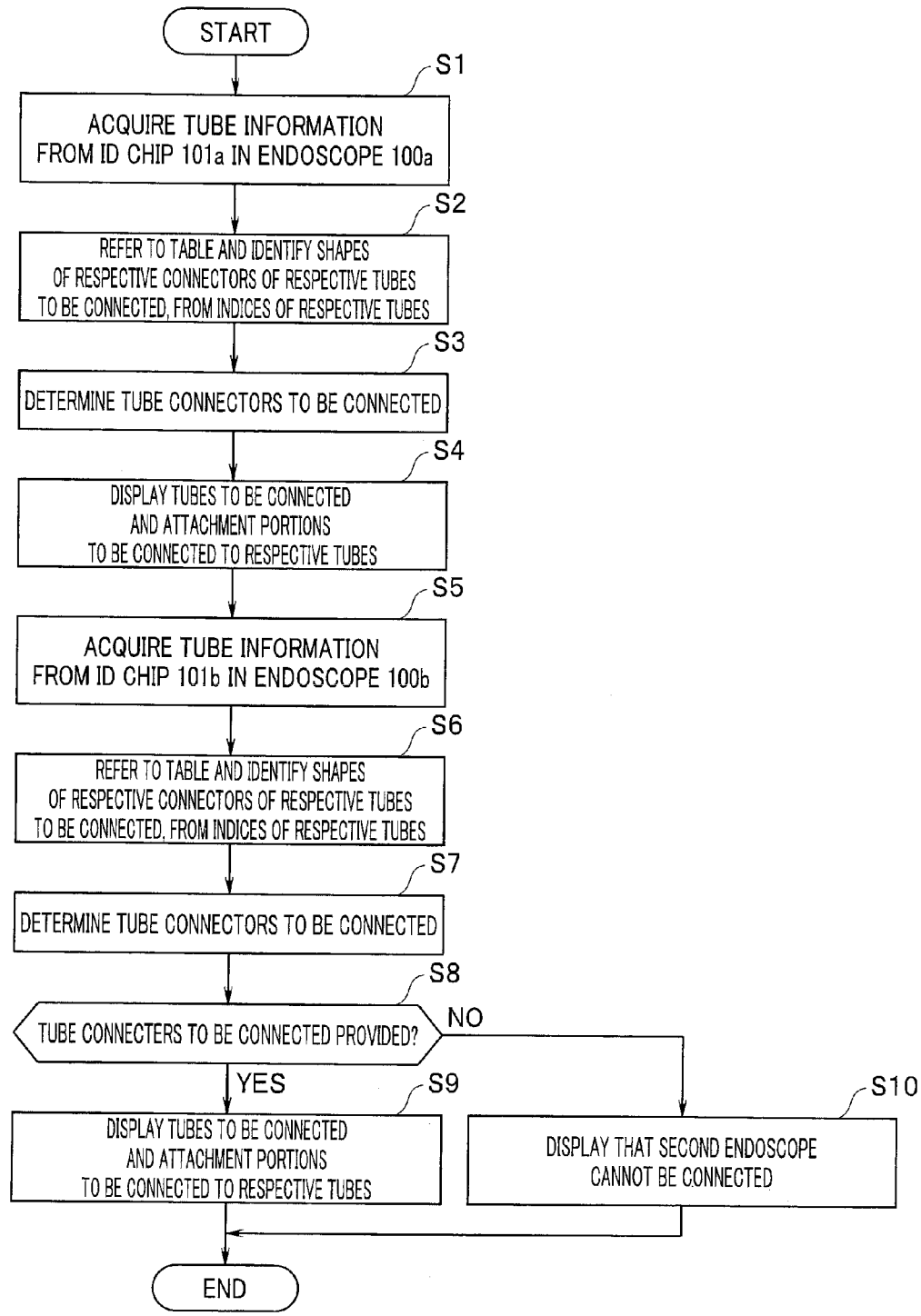
FIG. 11 is a flowchart for illustrating an example of cleaning/disinfecting tube connection processing.

FIG. 11 is a flowchart for illustrating an example of cleaning/disinfecting tube connection processing.

First, tube information is acquired from the ID chip 101a in the endoscope 100a (step S1). With reference to the table, a shape of a connector of each tube to be connected is identified from an index of the tube (step S2), and tube connectors to be connected are determined (step S3). The tubes to be connected and attachment to be connected to the respective tubes are displayed (step S4).

Next, tube information is acquired from the ID chip 101b in the endoscope 100b (step S5). With reference to the table, a shape of a connector of each tube to be connected is identified from an index of the tube (step S6), and tube connectors to be connected are determined (step S7).

Next, whether or not the tube connectors to be connected are present is determined (step S8). If it is determined that the tube connectors to be connected are present, the result of the determination is YES, and the tubes to be connected and the attachment portions to be connected to the respective tubes are displayed (step S9), and the processing ends. On the other hand, if it is determined that the tube connectors to be connected are not present, the result of the determination is NO, and it is displayed that the second endoscope 100b cannot be connected (step S10), and the processing ends.

The above processing enables a checker to easily recognize parts to which cleaning/disinfecting tubes are to be connected, enabling prevention of misconnection and reduction in time required for setting the endoscopes 100a and 100b in the cleaning/disinfecting apparatus 1.

(Fourth Embodiment)

Next, a fourth embodiment will be described.

Figure 12:
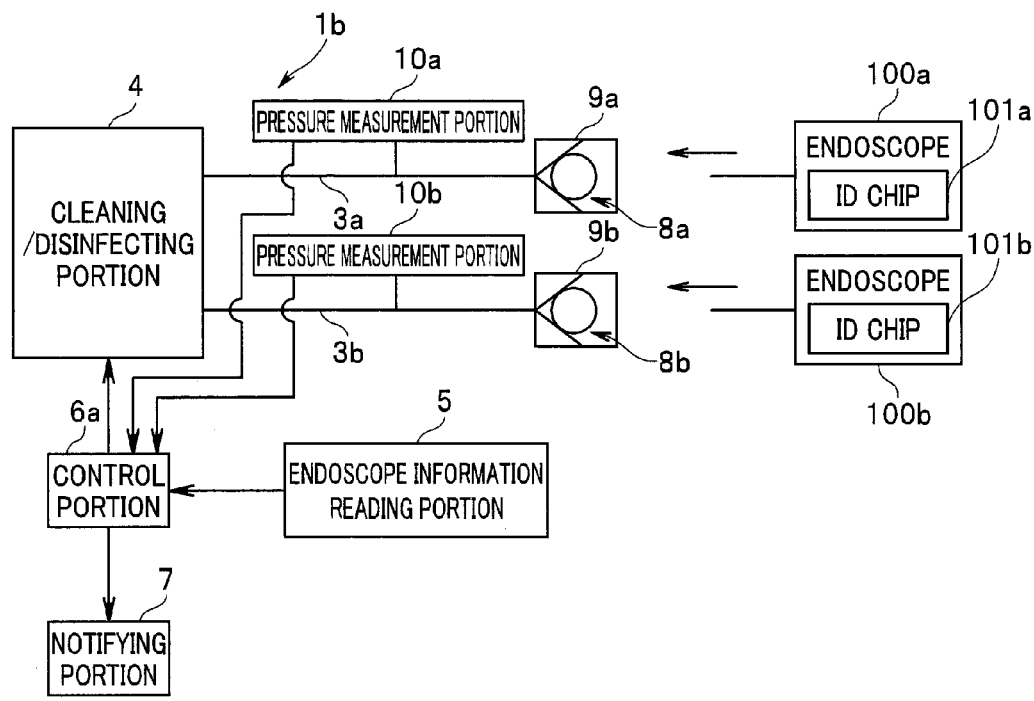
FIG. 12 is a diagram showing a configuration of a cleaning/disinfecting apparatus according to a fourth embodiment.

FIG. 12 is a diagram showing a configuration of a cleaning/disinfecting apparatus according to the fourth embodiment. It should be noted that in FIG. 12, same reference numerals are used for denoting the same components as those in FIG. 1, and descriptions thereof are omitted.

As shown in FIG. 12, a cleaning/disinfecting apparatus 1b includes a control portion 6a instead of the control portion 6 in FIG. 1. Also, in the cleaning/disinfecting apparatus 1b, an attachment portion 9a including a check valve 8a and an attachment portion 9b including a check valve 8b are provided at the distal ends of the conduits 3a and 3b, respectively. Also, in the cleaning/disinfecting apparatus 1b, pressure measurement portions 10a and 10b are provided at predetermined positions on the conduits 3a and 3b, respectively.

The check valve 8a is closed to achieve airtightness when an endoscope, for example, the endoscope 100a is not attached to the attachment portion 9a, and when the endoscope 100a is attached, the check valve 8a is opened. Similarly, the check valve 8b is closed to achieve airtightness when an endoscope, for example, the endoscope 100b is not attached to the attachment portion 9b, and when the endoscope 100b is attached, the check valve 8b is opened.

The pressure measurement portions 10a and 10b are electrically connected to the control portion 6a. The pressure measurement portions 10a and 10b measure pressures in the conduits 3a and 3b, respectively and output the measured pressure values to the control portion 6a.

In the present embodiment, if a power supply of the cleaning/disinfecting portion 4 is turned on, the cleaning/disinfecting portion 4 supplies gas such as air to the conduits 3a and 3b through a pump, not shown, based on the control of the control portion 6a to pressurize the conduits 3a and 3b up to a predetermined pressure P. It should be noted that the process for pressurizing up to the predetermined pressure P may also be executed after endoscope information is read by the endoscope information reading portion 5. The control portion 6a detects whether or not the pressures in the conduits 3a and 3b have reached the predetermined pressure P based on the pressure values in the conduits 3a and 3b inputted from the pressure measurement portions 10a and 10b. When the control portion 6a detects that the pressures in the conduits 3a and 3b have reached the predetermined pressure P, the control portion 6a stops the supply of gas from the cleaning/disinfecting portion 4.

If the endoscope 100a is attached to the attachment portion 9a to which a cleaning/disinfection menu for the endoscope 100a is assigned, the conduit 3a and a conduit in the endoscope 100a are communicated with each other, and the pressure in the conduit 3a is lowered. The lowered pressure value in the conduit 3a is outputted from the pressure measurement portion 10a to the control portion 6a.

The control portion 6a senses that the endoscope 100a is correctly connected to the attachment portion 9a by detecting the lowered pressure value in the conduit 3a. If the control portion 6a senses the correct connection, the control portion 6a outputs to the notifying portion 7 information indicating that the endoscope 100a is correctly connected to the attachment portion 9a and causes the notifying portion 7 to notify the information.

If the endoscope 100a is attached to the attachment portion 9b, to which a cleaning/disinfection menu for the endoscope 100a is not assigned, the conduit 3b and the conduit in the endoscope 100a are communicated with each other, and the pressure in the conduit 3b is lowered. The lowered pressure value in the conduit 3b is outputted from the pressure measurement portion 10b to the control portion 6a.

The control portion 6a senses that the endoscope 100a is erroneously connected to the attachment portion 9b, to which a cleaning/disinfection menu for the endoscope 100a is not assigned, by detecting the lowered pressure value in the conduit 3b. If the control portion 6a senses the erroneous connection, the control portion 6a outputs to the notifying portion 7 error information indicating that the endoscope 100a is not attached to the attachment portion 9a correctly and causes the notifying portion 7 to notify the information.

Next, an operation of the cleaning/disinfecting apparatus 1b having such a configuration will be described.

First, once the checker turns on a power supply, not shown, of the cleaning/disinfecting apparatus 1b, the conduits 3a and 3b are pressurized up to the predetermined pressure P. Next, the checker causes the endoscope information reading portion 5 to read the endoscope information recorded on the ID chip 101a of the endoscope 100a for which the cleaning/disinfection menu is executed. Thereby, the cleaning/disinfection menu for the endoscope 100a is assigned to the attachment portion 9a and attachment portion identifying information for identifying the assigned attachment portion 9a is outputted from the control portion 6a to the notifying portion 7. Then, the notifying portion 7 notifies the attachment portion identifying information.

If the checker correctly attaches the endoscope 100a to the attachment portion 9a based on the attachment portion identifying information notified by the notifying portion 7, the conduit 3a and the conduit of the endoscope 100a are communicated with each other, and the conduit 3a is decompressed. This pressure change is outputted from the pressure measurement portion 10a provided on the conduit 3a to the control portion 6a and the correct attachment of the endoscope 100a to the attachment portion 9a is recognized. Thus, based on the control of the control portion 6a, the notifying portion 7 notifies information indicating the correct attachment.

If the checker connects the endoscope 100a to the attachment portion 9b erroneously, the conduit 3b and the conduit of the endoscope 100a are communicated with each other, and the conduit 3b is decompressed. This pressure change is outputted from the pressure measurement portion 10b provided on the conduit 3b to the control portion 6a and the incorrect attachment of the endoscope 100a to the attachment portion 9a is recognized. That is, although the control portion 6a has instructed the checker to attach the endoscope 100a to the attachment portion 9a, since the pressure of the conduit 3b connected to the attachment portion 9b, not the pressure of the conduit 3a connected to the attachment portion 9a, is lowered, it is determined that the endo scope 100a is not correctly attached to the attachment portion 9a. Thus, based on the control of the control portion 6a, the notifying portion 7 notifies error information indicating the incorrect attachment.

As hereinbefore described, since the cleaning/disinfecting apparatus 1b can automatically determine whether the two endoscopes 100a and 100b are correctly attached to the assigned attachment portions 9a and 9b, a cleaning/disinfection menu in an erroneous connection state can be prevented. Also, if the cleaning/disinfecting apparatus 1b senses an erroneous connection, since the notifying portion 7 notifies error information, the checker can easily find the erroneous connection.

(Modification 1 of Fourth Embodiment)

As a modification of the fourth embodiment, there may be a constitution including one openable/closable valve between the pressure measurement portion 10a and the cleaning/disinfecting portion 4, and another between the pressure measurement portion 10b and the cleaning/disinfecting portion 4. Further, it is desirable that the control portion 6a be able to control the valves.

The pressure in each of the conduits 3a and 3b pressurized by the pump can be maintained in a predetermined pressurized state by closing each of the check valves 8a and 8b.

As an example of a use of the valves, since the supply of gas from the cleaning/disinfecting portion 4 can be stopped by closing the valve, when the pressure measurement portions 10a and 10b detect that the pressures in the conduits 3a and 3b reach the predetermined pressure P and the control portion 6a receives a signal of the fact, the control portion 6a may send a signal to close each valve, thereby stopping the supply of gas from the cleaning/disinfecting portion 4.

(Modification 2 of Fourth Embodiment)

As another modification of the fourth embodiment, there may be connection sensing that uses the pressure measurement portions 10a and 10b. A pressure determining portion which can determine whether the pressure in the conduit 3a or 3b reaches a predetermined pressure is provided at a side of the pressure measurement portions 10a and 10b or at a side of the control portion 6a, and thereby an abnormality of the valves, the check valves 8a and 8b, or the conduits 3a and 3b as well as a connection abnormality between the check valves 8a, 8b and the endoscopes 100a, 100b can be sensed.

Specifically, the pressure determining portion is configured to be able to compare a normal pressure with pressures measured by the pressure measurement portions 10a and 10b, and if the pressure created when the valves and the check valves 8a, 8b are closed is lower than the normal pressure within a predetermined range, a gas leak due to a failure of the valves, the check valves 8a, 8b, or the conduits 3a, 3b can be sensed. Also, a gas leak due to improper engagement of the check valves 8a, 8b with the endoscopes 100a, 100b can be sensed.

If such an abnormality is sensed, the notifying portion 7 may also be used to notify the abnormality.

(Fifth Embodiment)

Next, a fifth embodiment will be described.

Figure 13:
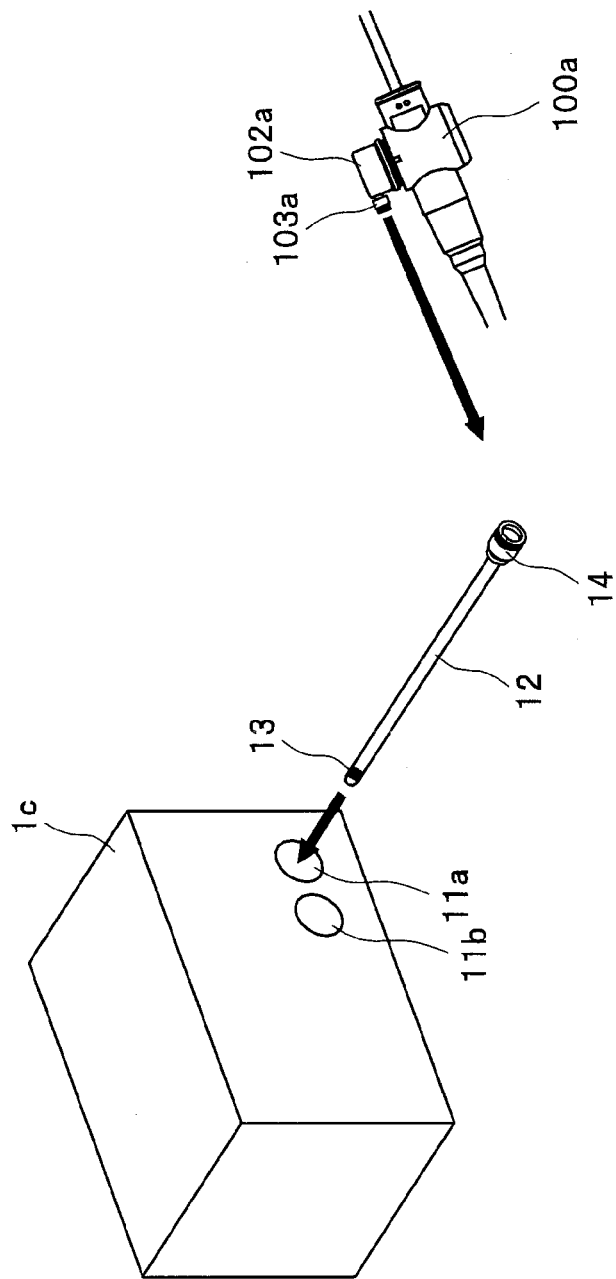
FIG. 13 is a diagram showing a configuration of a cleaning/disinfecting apparatus according to a fifth embodiment.

FIG. 13 is a diagram showing a configuration of a cleaning/disinfecting apparatus according to the fifth embodiment. It should be noted that in FIG. 13, same reference numerals are used for denoting the same components as those in FIG. 12, and descriptions thereof are omitted.

As shown in FIG. 13, a cleaning/disinfecting apparatus 1c includes a plurality of, here, two connection ports 11a and 11b for connecting a tube 12 used to connect the endoscope 100a with the cleaning/disinfecting apparatus 1c. It should be noted that since the connection ports 11a and 11b have the same configuration, hereinafter, only the connection port 11a will be described. One end of the tube 12 is provided with a connection pipe sleeve 13 to be connected with cleaning/disinfecting apparatus 1c. Also, the other end of the tube 12 is provided with an endoscope pipe sleeve 14 to be connected with a waterproof pipe sleeve 103a of a waterproof cap 102a covering the endoscope 100a or an electrical connector of the endoscope 100a.

Figure 14:
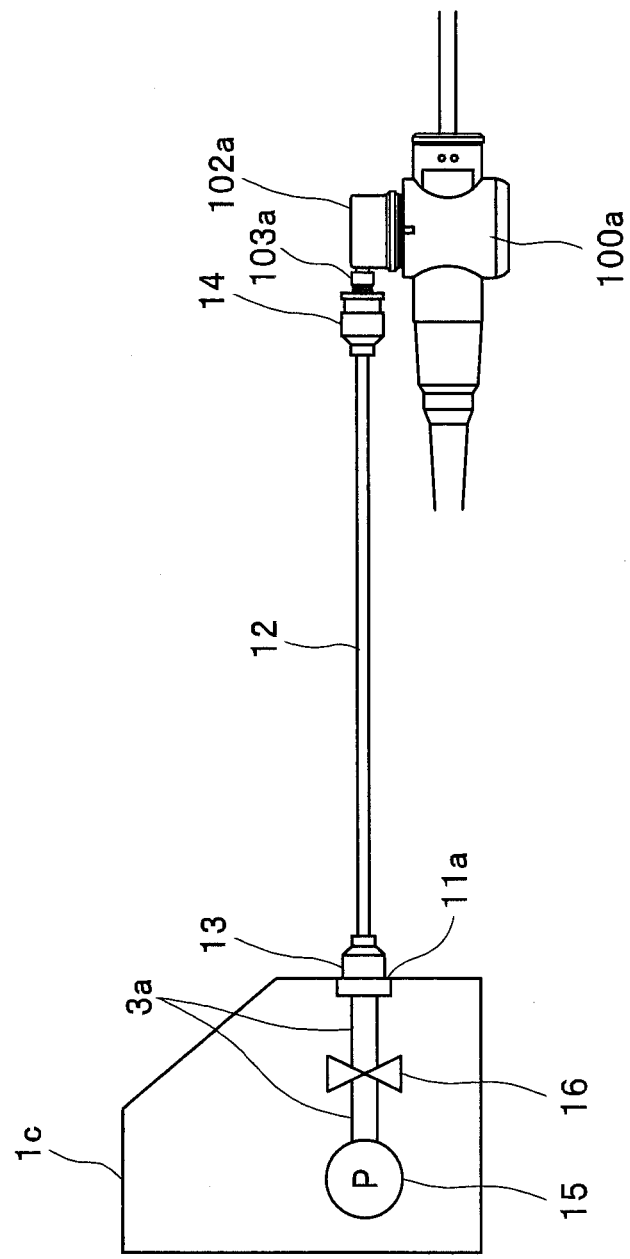
FIG. 14 is a diagram for illustrating an internal configuration of the cleaning/disinfecting apparatus according to the fifth embodiment.

FIG. 14 is a diagram for illustrating an internal configuration of the cleaning/disinfecting apparatus according to the fifth embodiment.

As shown in FIG. 14, in the cleaning/disinfecting apparatus 1c, a rear end of the connection port 11a is connected with the conduit 3a, and a rear end of the conduit 3a is connected with a pump 15. Also, a cutoff valve 16 is provided midway along the conduit 3a.

In such a configuration, if the connection pipe sleeve 13 of the tube 12 is connected with the connection port 11a, and the endoscope pipe sleeve 14 is connected with the waterproof pipe sleeve 103a, the conduit 3a from the cutoff valve 16 to the connection port 11a, the inside of the tube 12, and an airtight area of the endoscope 100a are connected to each other, and they are maintained airtight.

Now, a detailed configuration of the connection port and the connection pipe sleeve will be described with reference to FIG. 15 and FIG. 16.

Figure 15:
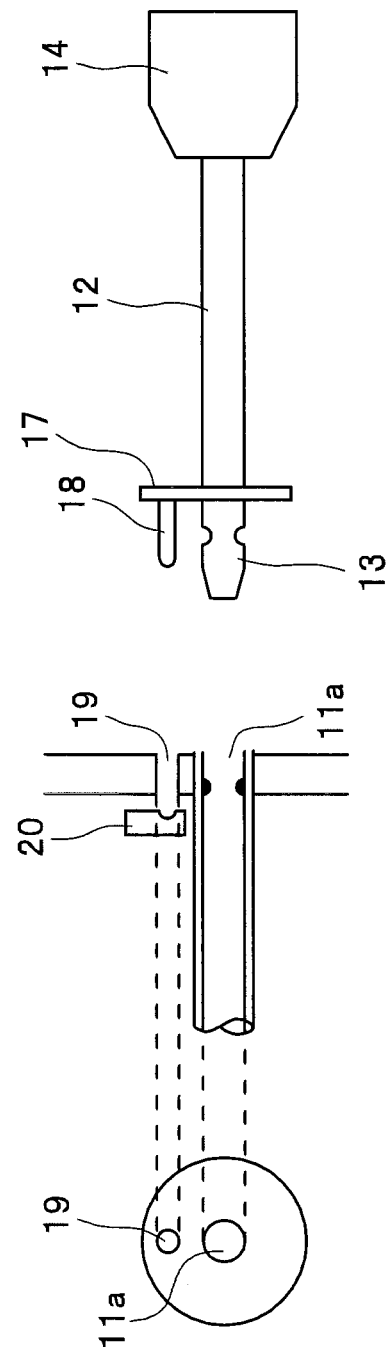
FIG. 15 is a diagram for illustrating a detailed configuration of a connection port and a connection pipe sleeve.
Figure 16:
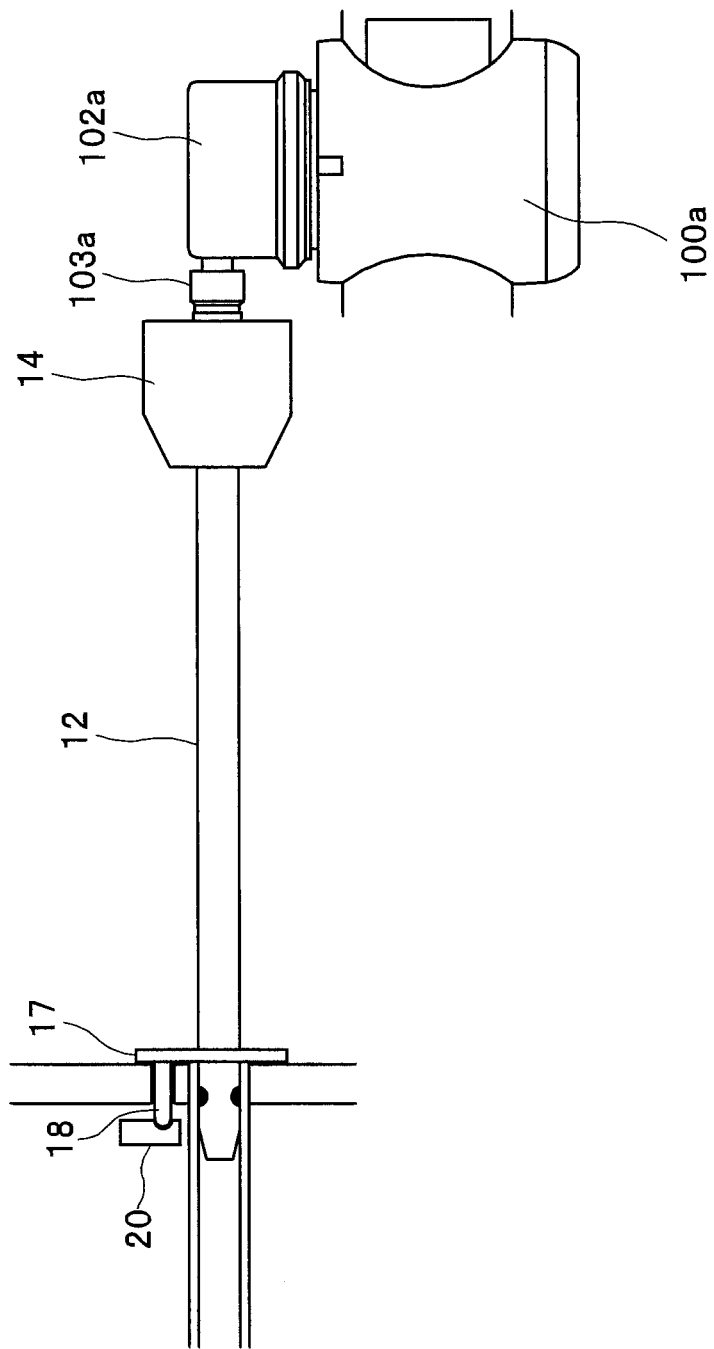
FIG. 16 is a diagram for illustrating a condition where the connection port and the connection pipe sleeve are connected with each other.

FIG. 15 is a diagram for illustrating the detailed configuration of the connection port and the connection pipe sleeve, and FIG. 16 is a diagram for illustrating a condition where the connection port and the connection pipe sleeve are connected with each other.

As shown in FIG. 15, a flange 17 is provided near the connection pipe sleeve 13 of the tube 12. At a predetermined position on the flange 17, a protrusion portion 18 pointing to the cleaning/disinfecting apparatus 1c is provided in parallel with a longitudinal axis direction of the tube 12.

On the other hand, a protrusion portion insertion opening 19 is provided above the connection port 11a of the cleaning/disinfecting apparatus 1c, and the opening 19 is shaped so that the protrusion portion 18 is inserted therein when the connection pipe sleeve 13 is connected to the connection port 11a. On a rear side of the protrusion portion insertion opening 19, a press button switch 20 is provided at a position which the protrusion portion 18 can push as shown in FIG. 16 when the connection pipe sleeve 13 is connected with the connection port 11a so as to achieve airtightness.

The press button switch 20 is electrically connected to the control portion 6a and outputs a depression sensed signal indicating whether the press button switch 20 is depressed by the protrusion portion 18 to the control portion 6a. Thereby, the control portion 6a determines whether or not the endoscope 100a is correctly connected with the connection port 11a and causes the notifying portion 7 to notify a determination result.

It should be noted that the configuration for sensing the connection between the connection port 11a and the connection pipe sleeve 13 is not limited to the configuration of the protrusion portion 18 and the press button switch 20. For example, there may be a configuration for sensing connection by a protrusion portion blocking an optical axis of an optical sensor, a configuration for sensing connection by a metal protrusion portion and a metal sensor, a configuration for sensing connection by a magnetized metal protrusion portion and a magnetic sensor, and a configuration for sensing connection by an RFID antenna reading an RFID chip incorporated in a protrusion portion. In such a configuration, since there is no mechanical connection during the sensing, durability of the cleaning/disinfecting apparatus 1c is allowed to be improved.

Next, an operation of the cleaning/disinfecting apparatus 1c having such a configuration will be described.

First, the checker turns on a power supply, not shown, of the cleaning/disinfecting apparatus 1c and allows the endoscope information reading portion 5 to read endoscope information recorded on the ID chip 101a of the endoscope 100a for which the cleaning/disinfection menu is executed. In response, a cleaning/disinfection menu for the endoscope 100a is assigned to the connection port 11a. Next, the checker connects the endoscope pipe sleeve 14 to the waterproof pipe sleeve 103a and the connection pipe sleeve 13 to the assigned connection port 11a.

If the connection pipe sleeve 13 is connected with the connection port 11a, the press button switch 20 is depressed by the protrusion portion 18. A depression sensed signal is outputted from the press button switch 20 to the control portion 6a, and the control portion 6a determines whether or not the endoscope 100a is correctly connected. The notifying portion 7 notifies a determination result as to whether the endoscope 100a has been correctly connected. Because the other operations are similar to those in the fourth embodiment, a description thereof will be omitted.

As hereinbefore described, the cleaning/disinfecting apparatus 1c automatically recognizes whether the cleaning/disinfecting apparatus 1c and the tube 12 has been correctly connected to each other in response to a depression sensed signal from the press button switch 20, and notifies a result thereof. Therefore, erroneous connecting made by the checker can be reliably prevented.

Figure 17:
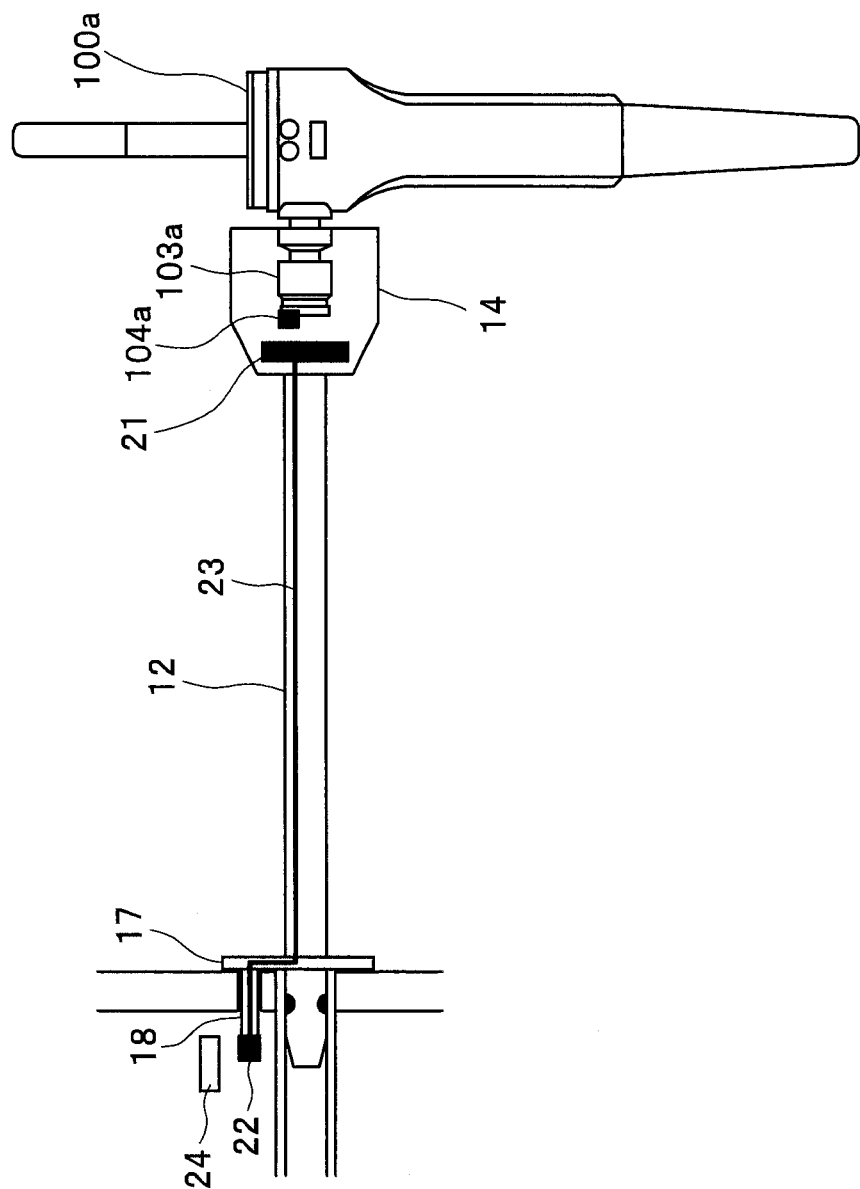
FIG. 17 is a diagram for illustrating connection of the cleaning/disinfecting apparatus, a tube, and an endoscope.

Note that, as a configuration for sensing that the cleaning/disinfecting apparatus 1c, the tube 12, and the endoscope 100a are reliably connected with each other, there may be a configuration as shown in FIG. 17.

FIG. 17 is a diagram for illustrating connection of the cleaning/disinfecting apparatus, the tube, and the endoscope.

As shown in FIG. 17, the endoscope 100a includes an ID chip 104a on which endoscope information is recorded near a distal end portion of the waterproof pipe sleeve 103a.

In the endoscope pipe sleeve 14 of the tube 12, an RFID antenna 21 is provided to, when the endoscope pipe sleeve 14 is connected with the waterproof pipe sleeve 103a, come close enough to read the endoscope information from the ID chip 104a. Also, a distal end of the protrusion portion 18 of the tube 12 is provided with an ID chip 22.

The RFID antenna 21 and the ID chip 22 are connected to each other via a communication cable 23 inserted in the tube 12, the flange 17, and the protrusion portion 18. The RFID antenna 21 can transmit the endoscope information read out from the ID chip 104a to the ID chip 22 through the communication cable 23.

In the cleaning/disinfecting apparatus 1c, an RFID antenna 24 is provided to, when the connection pipe sleeve 13 of the tube 12 is connected to the connection port 11a, come close enough to read the endoscope information transmitted to the ID chip 22. The RFID antenna 24 reads out the endoscope information transmitted from the RFID antenna 21 to the ID chip 22, and outputs the endoscope information to the control portion 6a.

According to such a configuration, when the endoscope pipe sleeve 14 and the waterproof pipe sleeve 103a are connected with each other, the RFID antenna 21 reads out the endoscope information recorded on the ID chip 104a and transmits the read-out endoscope information to the ID chip 22. Also, when the connection pipe sleeve 13 and the connection port 11a are connected with each other, the RFID antenna 24 reads out the endoscope information transmitted to the ID chip 22 and outputs the read-out endoscope information to the control portion 6a. As a result, the configuration can sense that the tube 12 is correctly connected with the cleaning/disinfecting apparatus 1c and the endoscope 100a. Also, if the correct connection is achieved, since the endoscope information on the endoscope 100a is automatically read out to the cleaning/disinfecting apparatus 1c, it is not necessary for the checker to cause the endoscope information reading portion 5 to read the endoscope information.

(Sixth Embodiment)

Next, a sixth embodiment will be described.

Figure 18:
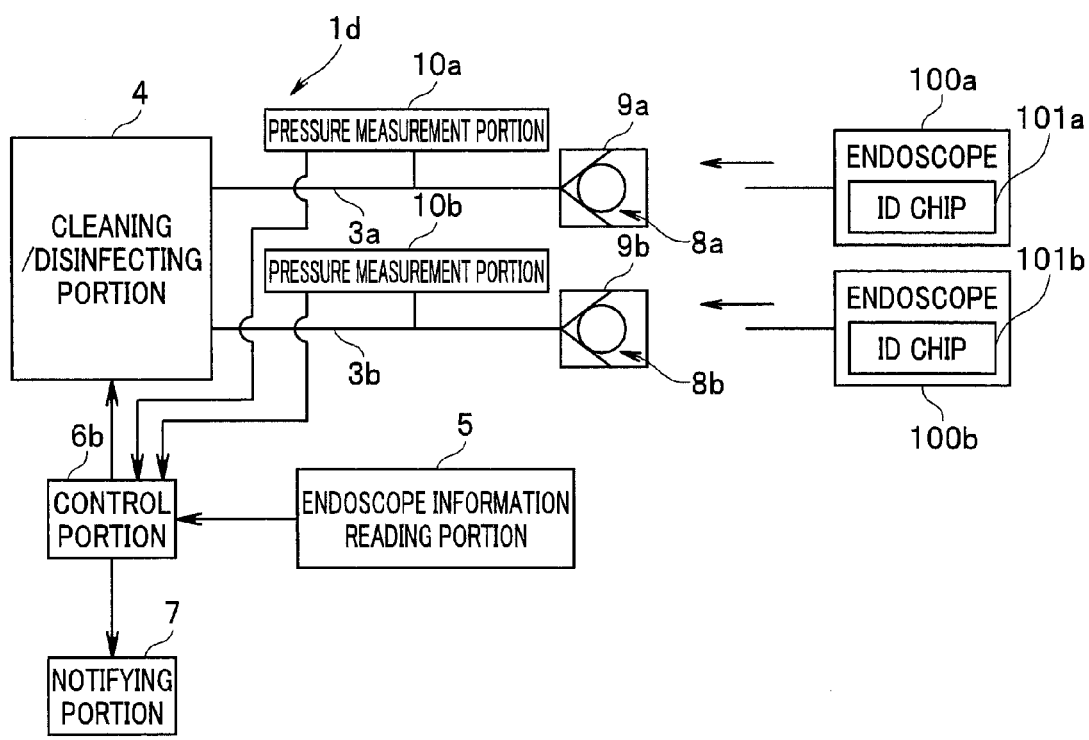
FIG. 18 is a diagram showing a configuration of a cleaning/disinfecting apparatus according to a sixth embodiment.

FIG. 18 is a diagram showing a configuration of a cleaning/disinfecting apparatus according to the sixth embodiment. It should be noted that in FIG. 18, same reference numerals are used for denoting the same components as those in FIG. 12, and descriptions thereof are omitted.

As shown in FIG. 18, a cleaning/disinfecting apparatus 1d includes a control portion 6b instead of the control portion 6a in FIG. 12.

Once a power supply is turned on, the control portion 6b instructs the cleaning/disinfecting portion 4 to pressurize only any one of the conduits 3a and 3b up to the predetermined pressure P. Here, it is assumed that the control portion 6b instructs the cleaning/disinfecting portion 4 to pressurize the conduit 3a. Then, when the control portion 6b reads out the endoscope information recorded on the ID chip 101a, the control portion 6b assigns a cleaning/disinfection menu for the endoscope 100a to the attachment portion 9a.

When the endoscope 100a is attached to the attachment portion 9a, the control portion 6b senses a pressure change from the pressure measurement portion 10a and recognizes that the correct connection has been achieved. If the control portion 6b recognizes that the correct connection has been achieved, the control portion 6b causes the cleaning/disinfecting portion 4 to execute the cleaning/disinfection menu assigned to the attachment portion 9a.

In contrast, if the endoscope 100a is attached to the attachment portion 9b, since the conduit 3b is not pressurized, the control portion 6b does not sense a pressure change from the pressure measurement portion 10b. The control portion 6b determines that the correct connection is not achieved for a period during which a pressure change is not sensed, and does not cause the cleaning/disinfecting portion 4 to execute the cleaning/disinfection menu.

Next, an operation of the cleaning/disinfecting apparatus 1d having such a configuration will be described.

First, when the checker turns on a power supply, not shown, of the cleaning/disinfecting apparatus 1d, any one of the conduits 3a and 3b, here, the conduit 3a is pressurized to the predetermined pressure P. Then, the checker allows the endoscope information reading portion 5 to read endoscope information recorded on the ID chip 101a of the endoscope 100a for which the cleaning/disinfection menu is executed. In response, a cleaning/disinfection menu for the endoscope 100a is assigned to the attachment portion 9a. Then, attachment portion identifying information for identifying the assigned attachment portion 9a is outputted from the control portion 6b to the notifying portion 7, and the notifying portion 7 notifies the attachment portion identifying information.

Once the checker attaches the endoscope 100a to the assigned attachment portion 9a, the conduit 3a connected with the attachment portion 9a is decompressed, and information about the pressure change is outputted from the pressure measurement portion 10a to the control portion 6b. The control portion 6b recognizes that the endoscope 100a is correctly attached to the attachment portion 9a based on the information about the pressure change, and causes the cleaning/disinfecting portion 4 to execute the cleaning/disinfection menu. In contrast, if pressure change information is not received (as input), the control portion 6b determines that the endoscope 100a is not correctly attached to the attachment portion 9a and does not cause the cleaning/disinfecting portion 4 to execute the cleaning/disinfection menu.

As hereinbefore described, if the endoscope 100a is not correctly attached to the attachment portion 9a, since the cleaning/disinfecting apparatus 1d does not cause the cleaning/disinfection menu to be executed, the cleaning/disinfection menu can be prevented from being executed in an erroneous connection state. Also, the checker is allowed to easily recognize erroneous connection because the cleaning/disinfection menu is not executed in an erroneous connection state.

(Seventh Embodiment)

Next, a seventh embodiment will be described.

Figure 20A:
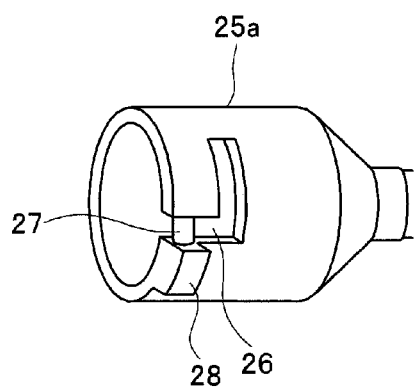
FIG. 20A is a diagram for illustrating a detailed configuration of an attachment portion.
Figure 20B:
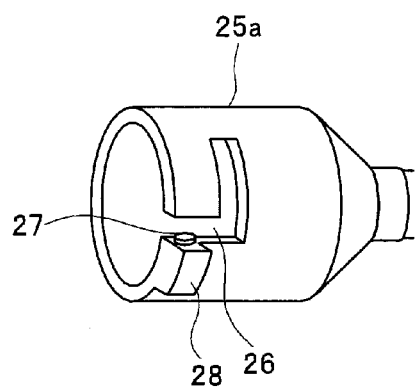
FIG. 20B is a diagram for illustrating a detailed configuration of the attachment portion.
Figure 21A:
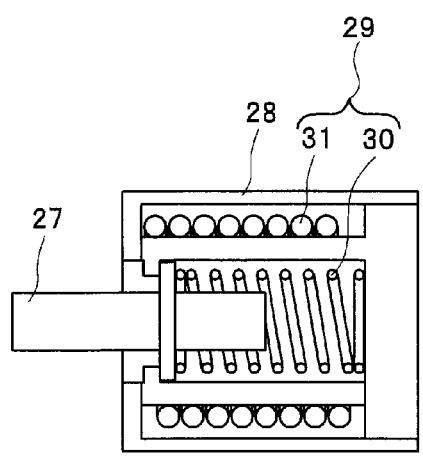
FIG. 21A is a cross-sectional view for illustrating a configuration of a solenoid housing portion.
Figure 21B:
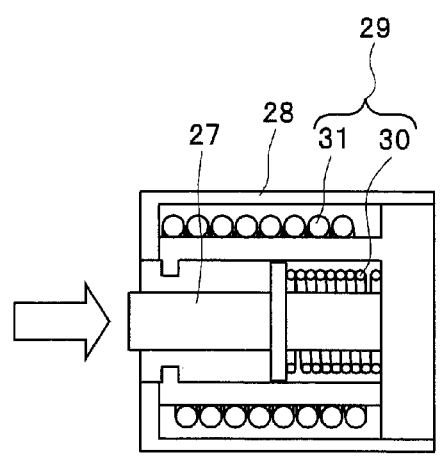
FIG. 21B is a cross-sectional view for illustrating a configuration of the solenoid housing portion.

FIG. 19 is a diagram showing a configuration of a cleaning/disinfecting apparatus according to the seventh embodiment, FIGS. 20A and 20B are diagrams for illustrating a detailed configuration of the attachment portion, FIGS. 21A and 21B are cross-sectional views for illustrating a configuration of the solenoid housing portion. It should be noted that in FIG. 19, same reference numerals are used for denoting the same components as those in FIG. 18, and descriptions thereof are omitted.

As shown in FIG. 19, a cleaning/disinfecting apparatus 1e includes a control portion 6c, an attachment portion 25a, and an attachment portion 25b instead of the control portion 6b, the attachment portion 9a, and the attachment portion 9b in FIG. 18. The attachment portions 25a and 25b are electrically connected with the control portion 6c.

As shown in FIG. 20A, a notch portion 26 is provided at the attachment portion 25a, and a pin 105a (see FIG. 19) provided on the waterproof pipe sleeve 103a of the endoscope 100a is fitted in the notch portion 26. Also, a solenoid housing portion 28 in which a solenoid 29 for moving a movable core 27 is housed is provided at the attachment portion 25a.

As shown in FIG. 21A, the solenoid 29 includes a spring 30 urging the movable core 27 and a coil 31 around the spring 30. If the coil 31 is not energized, an urging force of the spring 30 pushes out the movable core 27 to a distal end side, and as shown in FIG. 20A, the notch portion 26 is closed by the movable core 27.

In contrast, if the coil 31 is energized by the control of the control portion 6c, a magnetic force is generated, and the movable core 27 is retreated against the urging force of the spring 30 in a rear end side. Then, as shown in FIG. 20B, the notch portion 26 is opened. As such, the movable core 27 is an opening/closing portion that closes or opens the notch portion 26.

If a cleaning/disinfection menu for the endoscope 100a is assigned to the attachment portion 25a, the control portion 6c gives an instruction to open the notch portion 26 of the attachment portion 25a, that is, to energize the coil 31. In response, the control portion 6c opens the notch portion 26 of the attachment portion 25a. If the control portion 6c senses that the endoscope 100a is attached to the attachment portion 25a based on a pressure change from the pressure measurement portion 10a, the control portion 6c gives an instruction to de-energize the coil 31. In response, the control portion 6c closes the notch portion 26 of the attachment portion 25a by the movable core 27.

Next, an operation of the cleaning/disinfecting apparatus 1e having such a configuration will be described.

First, once the checker turns on a power supply, not shown, of the cleaning/disinfecting apparatus 1e, the conduits 3a and 3b is pressurized to the predetermined pressure P, and the pressure is maintained. The control portion 6c recognizes the pressure-maintained condition, instructs the notifying portion 7 to notify a message "Please let the endoscope information reading portion 5 read the ID chip," and causes the notifying portion 7 to execute the notification. Then, the checker causes the endoscope information reading portion 5 to read the endoscope information recorded in the ID chip 101a of the endoscope 100a. The control portion 6c assigns a cleaning/disinfection menu to one of the attachment portions 25a and 25b, in this example, to the attachment portion 25a.

The control portion 6c gives an instruction to open the notch portion 26 for the assigned attachment portion 25a. In response to the instruction from the control portion 6c, the coil 31 of the solenoid 29 of the attachment portion 25a is energized and the movable core 27 moves. As a result, the notch portion 26 of the attachment portion 25a is opened and the checker is allowed to attach the waterproof pipe sleeve 103a of the endoscope 100a to the attachment portion 25a.

If the endoscope 100a is connected with the attachment portion 25a in which the notch portion 26 is opened, since the conduit in the endoscope 100a communicates with a conduit in the attachment portion 25a, a pressure value in the conduit 3a is lowered. If the pressure change is sensed by the control portion 6c, the control portion 6c recognizes that the endoscope 100a is attached to the attachment portion 25a and gives an instruction to the attachment portion 25a to de-energize itself.

In response to the instruction from the control portion 6c, the coil 31 in the solenoid 29 is de-energized. As a result, the movable core 27 is pushed back by the force of the spring 30 of the solenoid 29, and thereby the notch portion 26 of the attachment portion 25a is closed. Thus, the waterproof pipe sleeve 103a of the endoscope 100a becomes unable to be detached from the attachment portion 25a. The checker repeats the foregoing operation for the endoscope 100b, thereby attaching the endoscope 100b to the attachment portion 25b.

When the control portion 6c recognizes that the two endoscopes 100a and 100b are attached to the attachment portions 25a and 25b, respectively, the control portion 6c instructs the cleaning/disinfecting portion 4 to execute a cleaning/disinfection menu depending on types of the endoscopes 100a and 100b, and allows the cleaning/disinfecting portion 4 to execute the cleaning/disinfection. Simultaneously, the control portion 6c instructs the notifying portion 7 to notify a message "Cleaning/disinfection menu in process," and causes the notifying portion 7 to execute the notification.

If the execution of the cleaning/disinfection menu is completed, the control portion 6c instructs the notifying portion 7 to notify a result of the cleaning/disinfection menu, and causes the notifying portion 7 to execute the notification. Simultaneously, the control portion 6c instructs the cleaning/disinfecting portion 4 to decompress the conduits 3a and 3b and allows the cleaning/disinfecting portion 4 to execute the decompression. As a result, the pressures in the conduits 3a and 3b become equal to an atmospheric pressure.

The control portion 6c recognizes that each of the conduits 3a and 3b has been decompressed based on pressure values from the pressure measurement portions 10a and 10b and instructs the attachment portions 25a and 25b to open the notch portion 26. The checker detaches the endoscopes 100a and 100b from the attachment portions 25a and 25b and terminates the cleaning/disinfection menu.

As hereinbefore described, the cleaning/disinfecting apparatus 1e opens/closes the notch portion 26 of each of the attachment portions 25a and 25b at a proper timing to physically interrupt the connection with the endoscopes 100a and 100b, and thereby erroneous connecting can be reliably prevented. As a result, even a checker who does not have a detailed knowledge of an operation method of the cleaning/disinfecting apparatus 1e can simply utilize the cleaning/disinfecting apparatus 1e.

(Eighth Embodiment)

Next, an eighth embodiment will be described.

Figure 22:
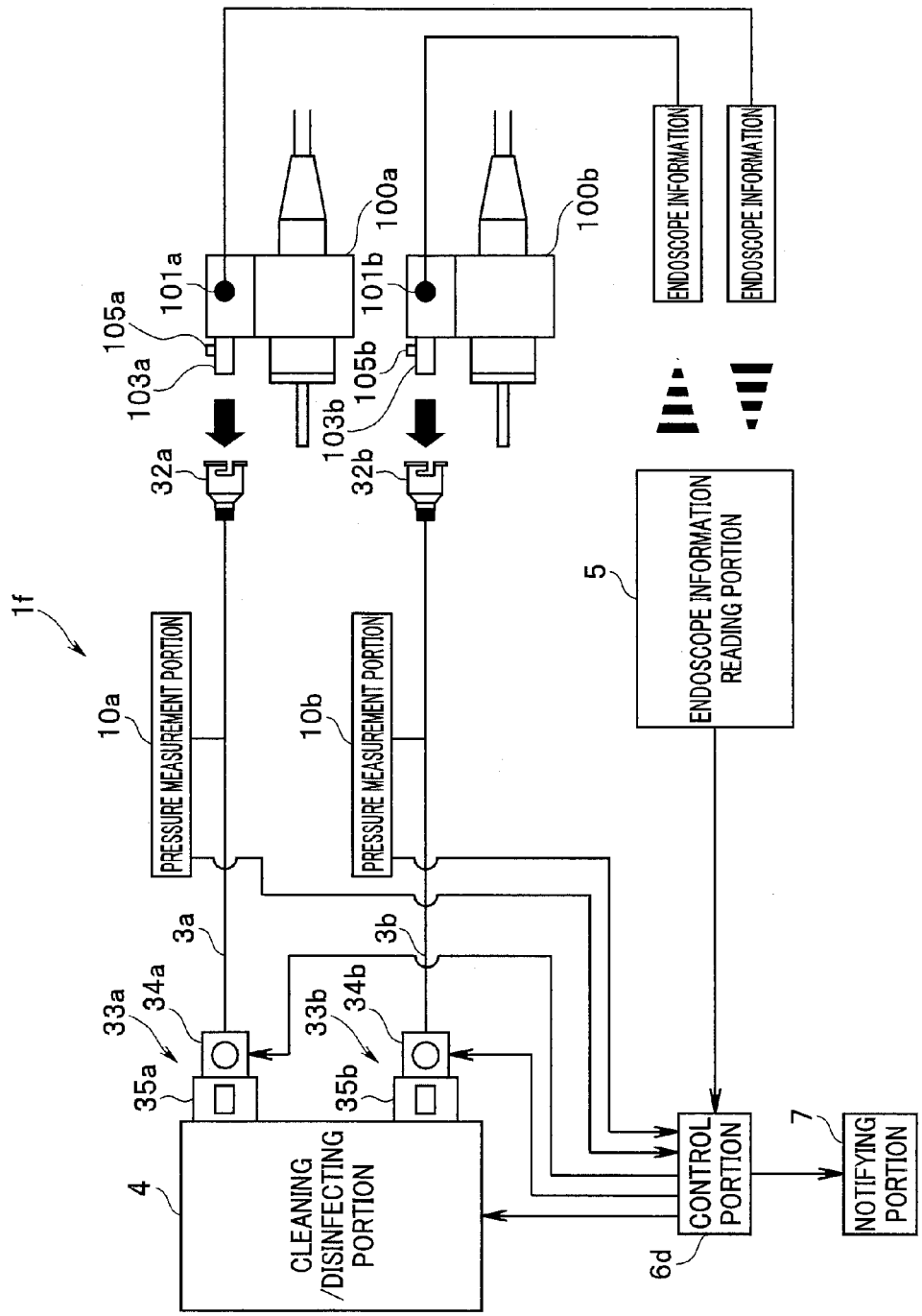
FIG. 22 is a diagram showing a configuration of a cleaning/disinfecting apparatus according to an eighth embodiment.
Figure 23:
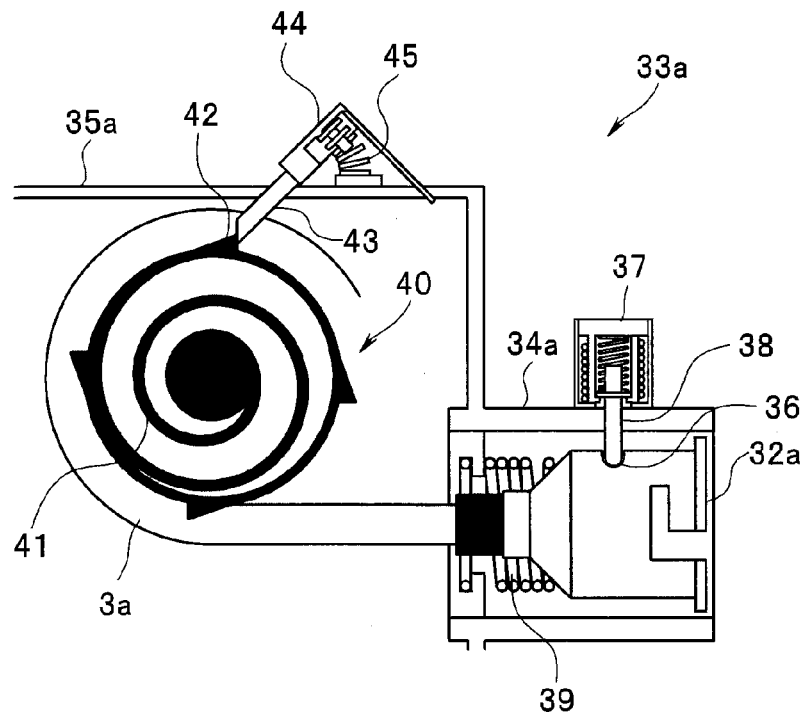
FIG. 23 is a diagram for illustrating a detailed configuration of a housing portion in which an attachment portion is housed.
Figure 24:
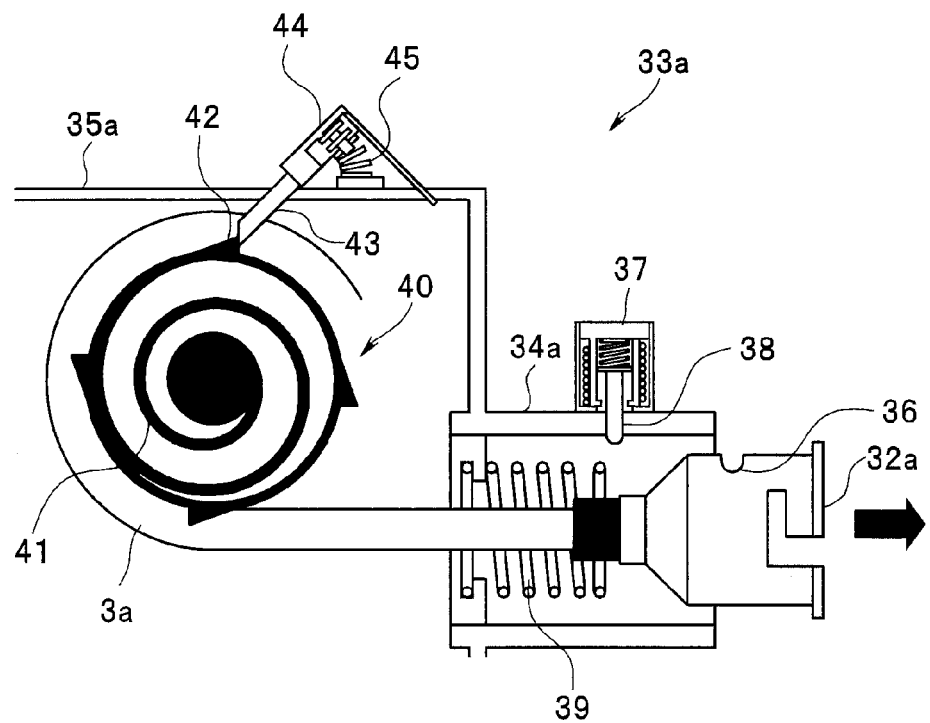
FIG. 24 is a diagram for illustrating a detailed configuration of the housing portion from which the attachment portion is taken out.
Figure 25:
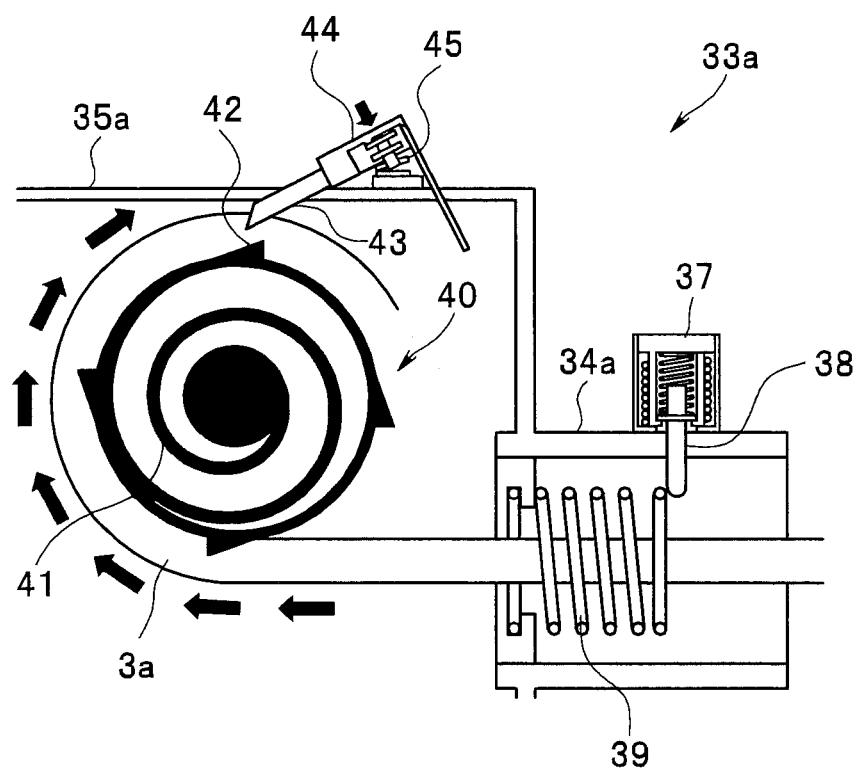
FIG. 25 is a diagram for illustrating a detailed configuration of the housing portion in which a conduit is wound.

FIG. 22 is a diagram showing a configuration of a cleaning/disinfecting apparatus according to the eighth embodiment, FIG. 23 is a diagram for illustrating a detailed configuration of a housing portion in which an attachment portion is housed, FIG. 24 is a diagram for illustrating a detailed configuration of the housing portion from which the attachment portion is taken out, and FIG. 25 is a diagram for illustrating a detailed configuration of the housing portion in which a conduit is wound. It should be noted that in FIG. 22, same reference numerals are used for denoting the same components as those in FIG. 19, and descriptions thereof are omitted.

As shown in FIG. 22, a cleaning/disinfecting apparatus 1f includes a control portion 6d, an attachment portion 32a, and an attachment portion 32b instead of the control portion 6c, the attachment portion 25a, and the attachment portion 25b in FIG. 19, respectively. Also, the cleaning/disinfecting portion 4 includes a housing portion 33a in which the conduit 3a and the attachment portion 32a are housed and a housing portion 33b in which the conduit 3b and the attachment portion 32b are housed.

In the attachment portion 32a, the movable core 27, the solenoid housing portion 28, and the solenoid 29 are removed from the attachment portion 25a in FIG. 19. And, as shown in FIG. 23, a notch portion 36 corresponding to a distal end shape of a movable core 38 is provided on an outer surface of the attachment portion 32a.

The housing portion 33a includes a distal end side housing portion 34a in which the attachment portion 32a is housed and a rear end side housing portion 35a in which the conduit 3a is housed. Similarly, the housing portion 33b includes a distal end side housing portion 34b in which the attachment portion 32b is housed and a rear end side housing portion 35b in which the conduit 3b is housed. It should be noted that because the housing portion 33a and the housing portion 33b have the same configuration, hereinafter, the housing portion 33a will be described.

As shown in FIG. 23, a solenoid 37 operated in response to an instruction from the control portion 6d is installed on a top surface of the distal end side housing portion 34a. When an internal coil is not energized in accordance with an instruction from the control portion 6d, the solenoid 37 pushes out a distal end downward by an urging force of a spring provided in the movable core 38. In contrast, when the internal coil is energized in accordance with an instruction from the control portion 6d, the solenoid 37 draws in the movable core 38 upward by a magnetic field generated by the coil.

In the distal end side housing portion 34a, a spring 39 exerting an urging force when the attachment portion 32a is housed is provided. As shown in FIG. 24, once the coil of the solenoid 37 is energized and the movable core 38 is detached from the notch portion 36, the attachment portion 32a is pushed forward from the housing portion 33a by an urging force of the spring 39.

Also, in the rear end side housing portion 35a, a winding portion 40 for winding the conduit 3a is provided. The winding portion 40 includes a winding spring 41 and claw-shaped protrusion portions 42. The attachment portion 32a and the conduit 3a are drawn out, and thereby tension is generated in the winding spring 41.

In order not to wind the conduit 3a by the tension of the winding spring 41, a stopper 43 is installed to be hooked by any of the protrusion portions 42. The stopper 43 is pushed against the winding portion 40 by an urging force of a spring 45 attached to a stopper release button 44 installed on a top surface of the rear end side housing portion 35a.

As shown in FIG. 25, when the stopper release button 44 is pressed, the stopper 43 comes off the protrusion portion 42 and the winding portion 40 is allowed to automatically wind the conduit 3a by the tension generated in the winding spring 41.

Next, an operation of the cleaning/disinfecting apparatus 1f having such a configuration will be described.

First, once the checker turns on a power supply, not shown, of the cleaning/disinfecting apparatus 1f, the conduits 3a and 3b are pressurized to the predetermined pressure P. Then, the checker allows the endoscope information reading portion 5 to read endoscope information recorded on the ID chip 101a of the endoscope 100a for which the cleaning/disinfection menu is executed.

The control portion 6d recognizes the endoscope information from the endoscope information reading portion 5 and gives an instruction to energize the coil of the solenoid 37 installed in the housing portion 33a in which the attachment portion 32a is housed. In response to an instruction from the control portion 6d, the coil of the solenoid 37 is energized and the movable core 38 of the solenoid 37 moves upward, thereby coming off the notch portion 36 formed on an outer surface of the attachment portion 32a. At this time, by an urging force of the spring 39 installed at a rear end side of the attachment portion 32a, the attachment portion 32a is pushed out of the housing portion 33a.

The checker connects the endoscope 100a with the pushed-out attachment portion 32a. At this time, since the inside of the endoscope 100a communicates with the conduit in the attachment portion 32a, a pressure value in the conduit 3a is lowered.

The control portion 6d recognizes that the endoscope 100a is connected with the attachment portion 32a based on the lowered pressure value and de-energizes the solenoid 37 installed in the housing portion 33a. The checker repeats the same operation for the unconnected endoscope 100b. Then, the checker attaches the endoscopes 100a and 100b to the attachment portion 32a and 32b, respectively and executes the cleaning/disinfection menu similarly to the seventh embodiment.

As hereinbefore described, the cleaning/disinfecting apparatus 1f is configured to read endoscope information and push out the attachable attachment portion 32a or 32b from the housing portion 33a or 33b. As a result, in the cleaning/disinfecting apparatus 1f, since the checker is allowed to visually make sure of the attachable attachment portion 32a or 32b, erroneous connecting can be reliably prevented.

Also, in the cleaning/disinfecting apparatus 1f, the conduits 3a and 3b, and the attachment portions 32a and 32b are allowed to be housed in the cleaning/disinfecting portion 4, so that space saving can be achieved compared with the cleaning/disinfecting apparatus 1e according to the seventh embodiment.

(Ninth Embodiment)

Figure 26:
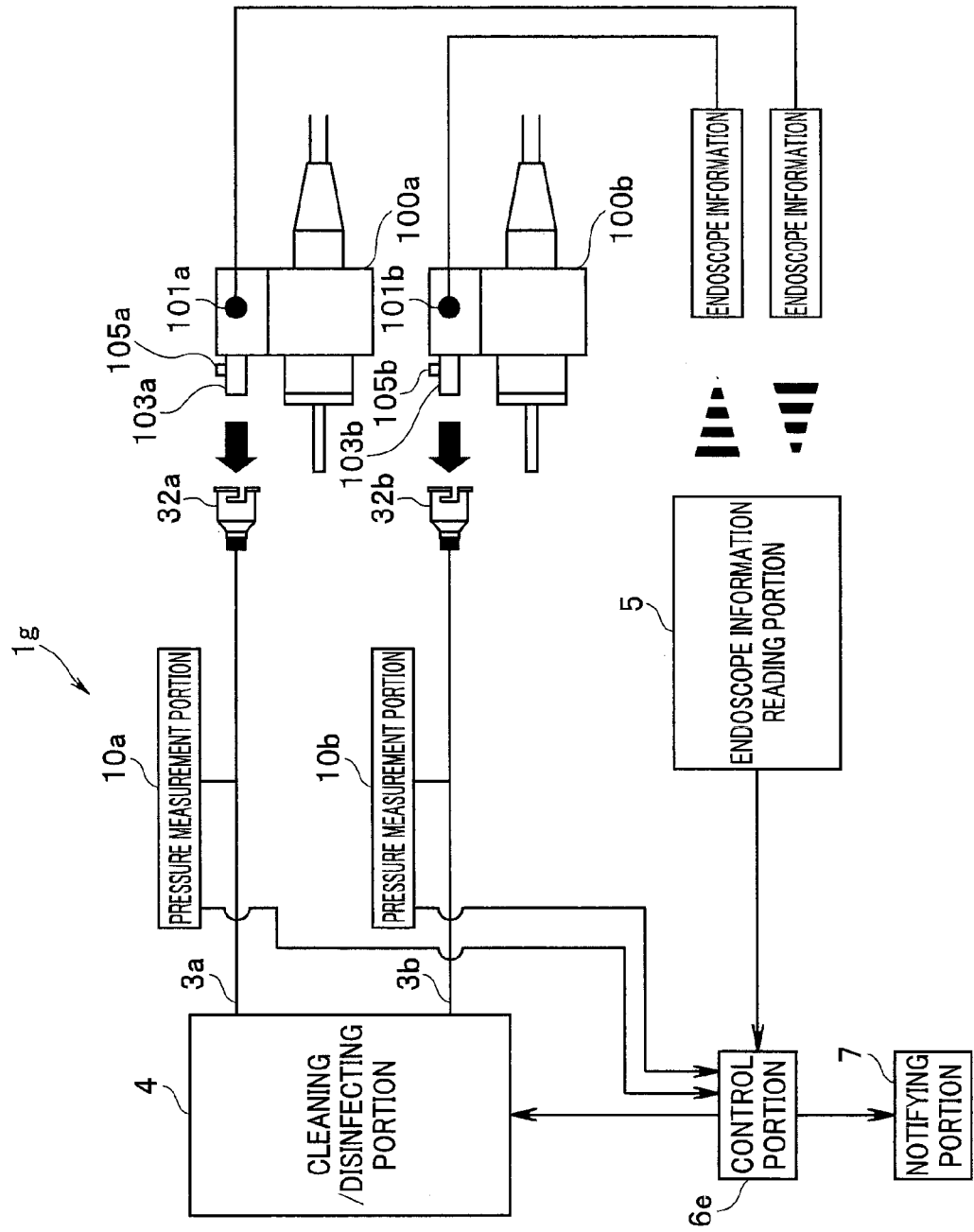
FIG. 26 is a diagram showing a configuration of a cleaning/disinfecting apparatus according to a ninth embodiment.

FIG. 26 is a diagram showing a configuration of a cleaning/disinfecting apparatus according to a ninth embodiment. It should be noted that in FIG. 26, same reference numerals are used for denoting the same components as those in FIG. 22, and descriptions thereof are omitted.

As shown in FIG. 26, a cleaning/disinfecting apparatus 1g includes a control portion 6e instead of the control portion 6d in FIG. 22 as well as the housing portions 33a and 33b are removed from FIG. 12.

When a power supply is turned on, the control portion 6e outputs an instruction to the cleaning/disinfecting portion 4 for setting the conduit 3a to a predetermined pressure P1, and the conduit 3b to a predetermined pressure P2. Here, the predetermined pressure P1 is pressure under which a human force is enough for attaching the endoscope 100a to the attachment portion 32a. And, the predetermined pressure P2 is pressure under which the endoscope 100a cannot be attached to the attachment portion 32a by a human force. The cleaning/disinfecting portion 4 supplies gas such as air from a pump or the like, not shown, to the conduits 3a and 3b based on an instruction from the control portion 6e.

When the control portion 6e senses that the conduit 3a reaches the predetermined pressure P1 based on a measurement value from the pressure measurement portion 10a, for example, the control portion 6e closes an electromagnetic valve, not shown, provided in the conduit 3a to maintain the pressure in the conduit 3a to the predetermined pressure P1. Also, when the control portion 6e senses that the conduit 3b reaches the predetermined pressure P2 based on a measurement value from the pressure measurement portion 10b, the control portion 6e maintains the pressure in the conduit 3b to the predetermined pressure P2.

Then, if the endoscope information reading portion 5 reads the endoscope information on the endoscope 100a, the control portion 6e causes the notifying portion 7 to notify the checker to attach the endoscope 100a to the attachment portion 32a, the pressure in which is maintained at the predetermined pressure P1, under which a human force is enough for the attachment.

Now, an operation of the cleaning/disinfecting apparatus 1g having such a configuration will be described with reference to FIG. 27.

Figure 27:
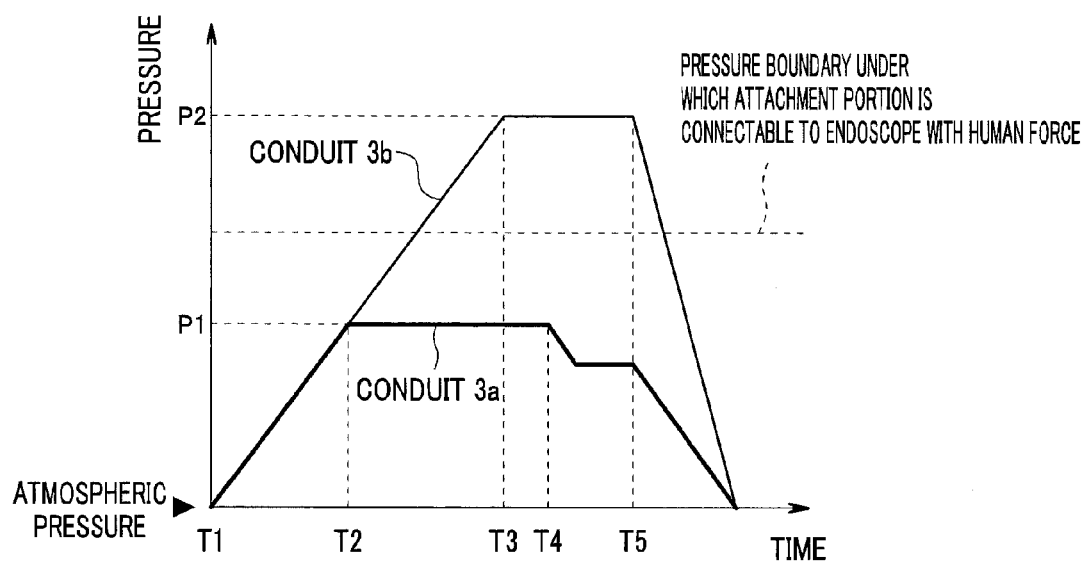
FIG. 27 is a diagram for illustrating an operation of a cleaning/disinfecting apparatus 1g according to the ninth embodiment.

FIG. 27 is a diagram for illustrating the operation of the cleaning/disinfecting apparatus 1g according to the ninth embodiment.

First, once the checker turns on a power supply, not shown, of the cleaning/disinfecting apparatus 1g at a time T1, the control portion 6e operates a pump, not shown, of the cleaning/disinfecting portion 4 to pressurize the conduits 3a and 3b. The control portion 6e performs sensing on a pressure value in the conduit 3a from the pressure measurement portion 10a and stops pressurizing the conduit 3a at a time T2 when the predetermined pressure P1 is achieved. Thereby, the pressure in the conduit 3a is maintained at the predetermined pressure P1.

Then, the control portion 6e operates the pump also after the time T2 to further pressurize the conduit 3b. The control portion 6e performs sensing on a pressure value in the conduit 3b from the pressure measurement portion 10b and stops pressurizing the conduit 3b at a time T3 when the predetermined pressure P2 is achieved. Thereby, the pressure in the conduit 3b is maintained at the predetermined pressure P2.

The checker causes the endoscope information reading portion 5 to read the endoscope information recorded on the ID chip 101a of the endoscope 100a. The control portion 6e allows the notifying portion 7 to notify the checker to connect the endoscope 100a to the attachment portion 32a, to which the endoscope 100a can be attached. Based on the information of which the checker is notified by the notifying portion 7, the checker attaches the endoscope 100a to the attachment portion 32a at a time T4. If the checker attempts to attach the endoscope 100a to the attachment portion 32b, since the conduit 3b has the predetermined pressure P2, at which the attachment cannot be achieved by a human force, erroneous connection cannot be executed. If the checker attaches the endoscope 100a to the attachment portion 32a, since the inside of the endoscope 100a communicates with the conduit in the attachment portion 32a, the pressure in the conduit 3a is lowered. The control portion 6e detects the pressure change and recognizes that the endoscope 100a has been correctly attached to the attachment portion 32a.

Then, at a time T5, the checker causes the endoscope information reading portion 5 to read the endoscope information recorded on the ID chip 101b of the endoscope 100b. When the control portion 6e receives the endoscope information from the endoscope information reading portion 5 (as input), the control portion 6e decompresses the conduits 3a and 3b to the atmospheric pressure. Thereby, the checker is allowed to attach the endoscope 100b to the attachment portion 32b connected with the conduit 3b. Then, the checker attaches the endoscopes 100a and 100b to the attachment portion 32a and 32b, respectively and executes the cleaning/disinfection menu similarly to the seventh embodiment.

As hereinbefore described, the cleaning/disinfecting apparatus 1g pressurizes one of the conduits 3a and 3b to the predetermined pressure P2, under which the attachment cannot be achieved by a human force, thereby disenabling attachment of an endoscope to one of the attachment portions 32a and 32b. As a result, the cleaning/disinfecting apparatus 1g can reliably prevent erroneous connection.

Further, the mechanical constitution of the cleaning/disinfecting apparatus 1g can be simplified compared with the cleaning/disinfecting apparatus 1e and 1f in the seventh and the eighth embodiments, so that the cleaning/disinfecting apparatus 1g can be provided costing less.

Incidentally, a cleaning/disinfecting apparatus 1 has a function that records reprocessing information (cleaning/disinfection information) in, e.g., an internal memory and outputs the reprocessing information via a printer. Then, a checker utilizes the sheet of paper outputted via the printer for reprocessing information management.

However, since the internal memory in the cleaning/disinfecting apparatus 1 has a limited capacity, it is difficult to record all pieces of reprocessing information for a period in which the cleaning/disinfecting apparatus 1 is used. Furthermore, paper-based reprocessing information management has a problem of a checker being unable to perform efficient reprocessing information management because of possibilities of deterioration, loss, etc., of the sheets of paper. Therefore, a history management unit that can facilitate reprocessing information management of the cleaning/disinfecting apparatus 1 will be described.

FIG. 28A is a perspective diagram of a history management unit as obliquely viewed from the front, and FIG. 28B is a perspective diagram of the history management unit as obliquely viewed from the back.

As illustrated in FIG. 28A, the history management unit 200 includes, at a front face thereof, a power supply switch 201, a communication lamp 202 that senses a state of communication with a cleaning/disinfecting apparatus 1, a port 203 to which a recording medium such as a USB memory can be connected, and a connection lamp 204 that senses a state of connection with the recording medium.

As illustrated in FIG. 28B, the history management unit 200 includes, at a rear face thereof, a power supply outlet 205 for connection with a power supply, and communication ports 206 and 207 for connection with the cleaning/disinfecting apparatus 1 and a personal computer.

FIGS. 29A, 29B and 29C are diagrams for illustrating data communications via a history management unit 200.

As illustrated in FIG. 29A, a history management unit 200 is connected to the cleaning/disinfecting apparatus 1 via a communication cable 208 such as an RS232C cable. Consequently, the history management unit 200 acquires reprocessing information from the cleaning/disinfecting apparatus 1 via the communication cable 208, and records the reprocessing information in a non-illustrated internal memory. The reprocessing information recorded in the history management unit 200 can be outputted to a recording medium 209 by connecting the recording medium 209 such as a USB memory to the port 203.

A file outputted to the recording medium 209 is in a versatile data format such as a CSV format. A checker can transfer data including reprocessing information to a personal computer 210 using the recording medium 209. And, as illustrated in FIG. 29B, it is possible that the cleaning/disinfecting apparatus 1 transfers reprocessing information to a history management unit 200 by means of wireless communication and the history management unit 200 transfers the reprocessing information to the personal computer 210 by means of wireless communication.

As illustrated in FIG. 29C, a history management unit 200 is connected to the cleaning/disinfecting apparatus 1 via a communication cable 208 such as an RS232C cable. Consequently, the history management unit 200 acquires reprocessing information from the cleaning/disinfecting apparatus 1 via the communication cable 208 and records the reprocessing information in the non-illustrated internal memory. The reprocessing information recorded in the history management unit 200 may be transferred to a PC 210 via a communication cable 215.

Consequently, the checker can perform reprocessing information management in the personal computer 210. Thus, the number of recorded pieces of reprocessing information can be increased, and the reprocessing information can be managed not on paper but as electronic data.

Figure 30:
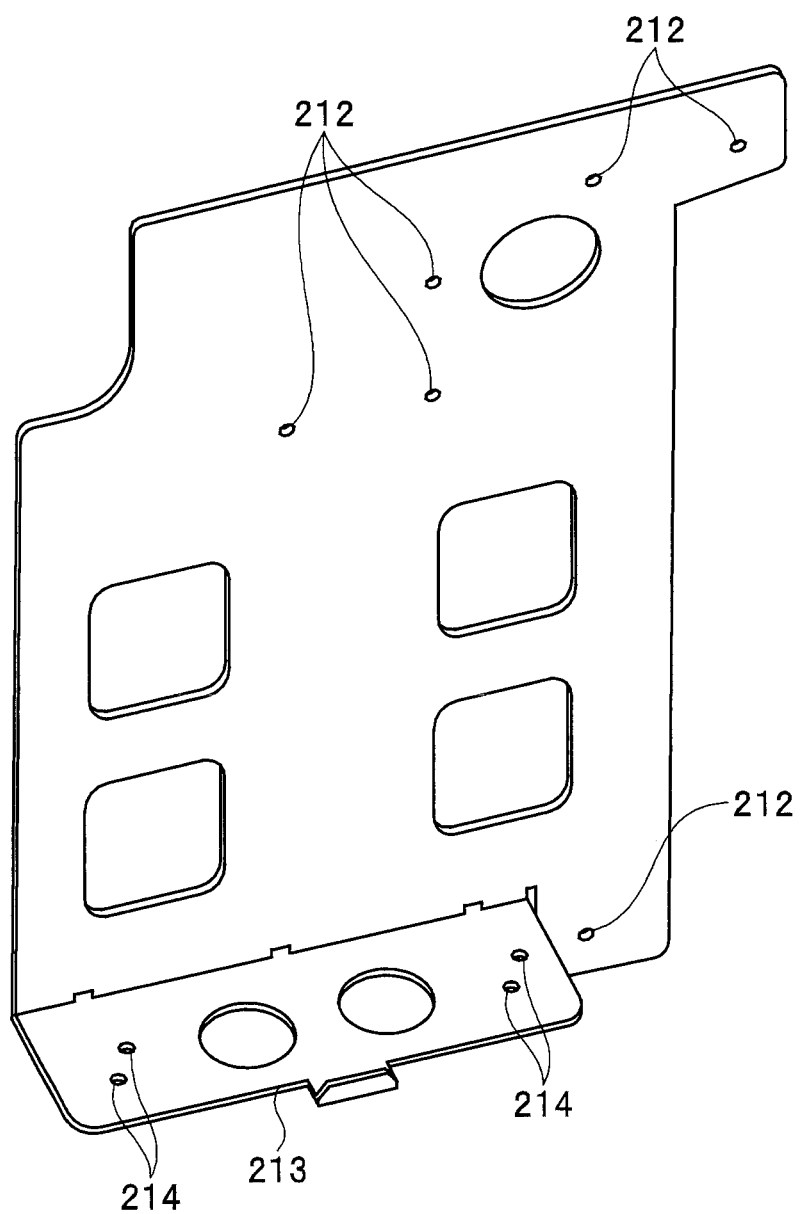
FIG. 30 is a diagram showing an example of a fixture for fixing a history management unit 200 to the cleaning/disinfecting apparatus 1.

Furthermore, the history management unit 200 is installed on a side face or a front face of the cleaning/disinfecting apparatus 1 using a dedicated fixture, which is illustrated in FIG. 30, enabling space saving.

FIG. 30 is a diagram showing an example of a fixture for fixing a history management unit 200 to the cleaning/disinfecting apparatus 1.

As illustrated in FIG. 30, a fixture 211 is formed in an L shape. Although a material for the fixture is not specifically limited, if the fixture is formed by a metal, stainless steel can be used. In an upper part of the fixture 211, a plurality of screw holes 212 are provided, and the upper part is fixed to a side face of the cleaning/disinfecting apparatus 1 via non-illustrated in screws. Also, in a bottom face 213 of the fixture 211, a plurality of screw holes 214 are provided. A history management unit 200 is put on the bottom face 213 of the fixture 211 and fixed to the fixture 211 via non-illustrated screws.

Figure 31:
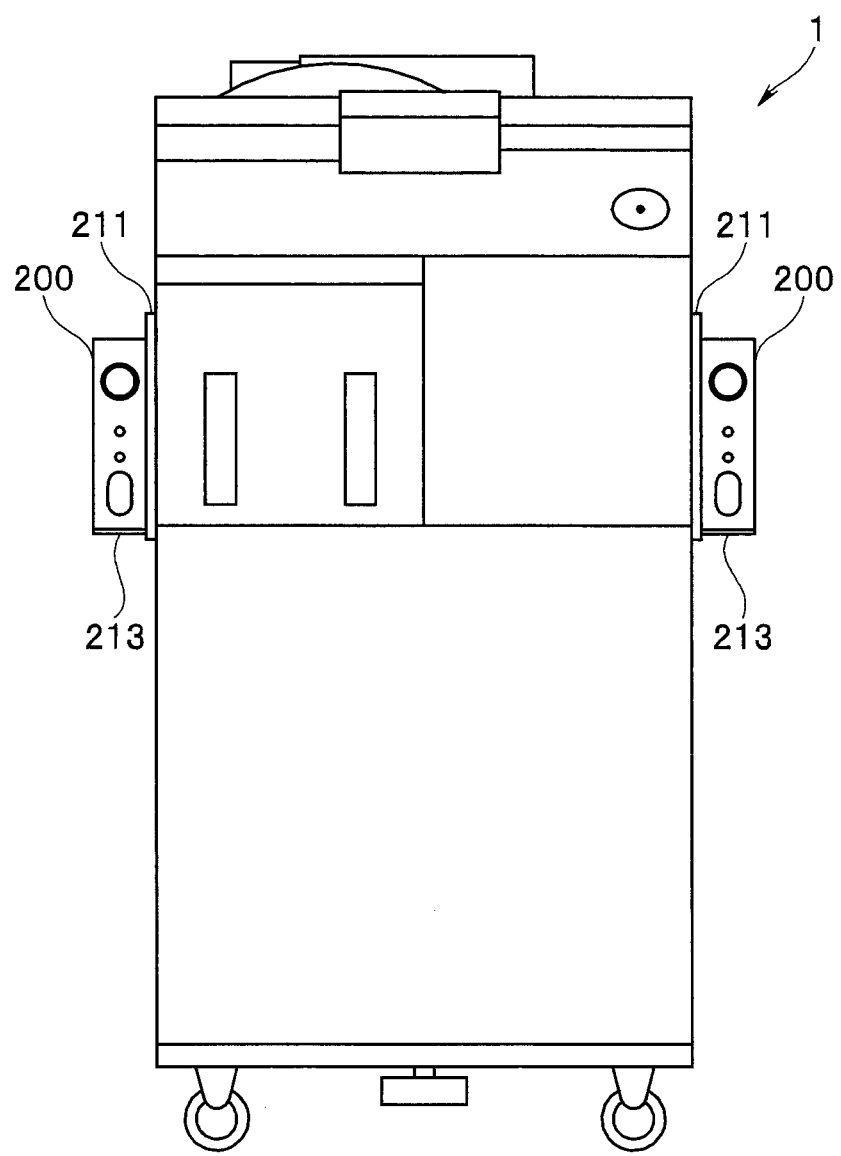
FIG. 31 is a diagram showing a state in which a history management unit 200 is installed on each of opposite side faces of the cleaning/disinfecting apparatus 1.
Figure 32:
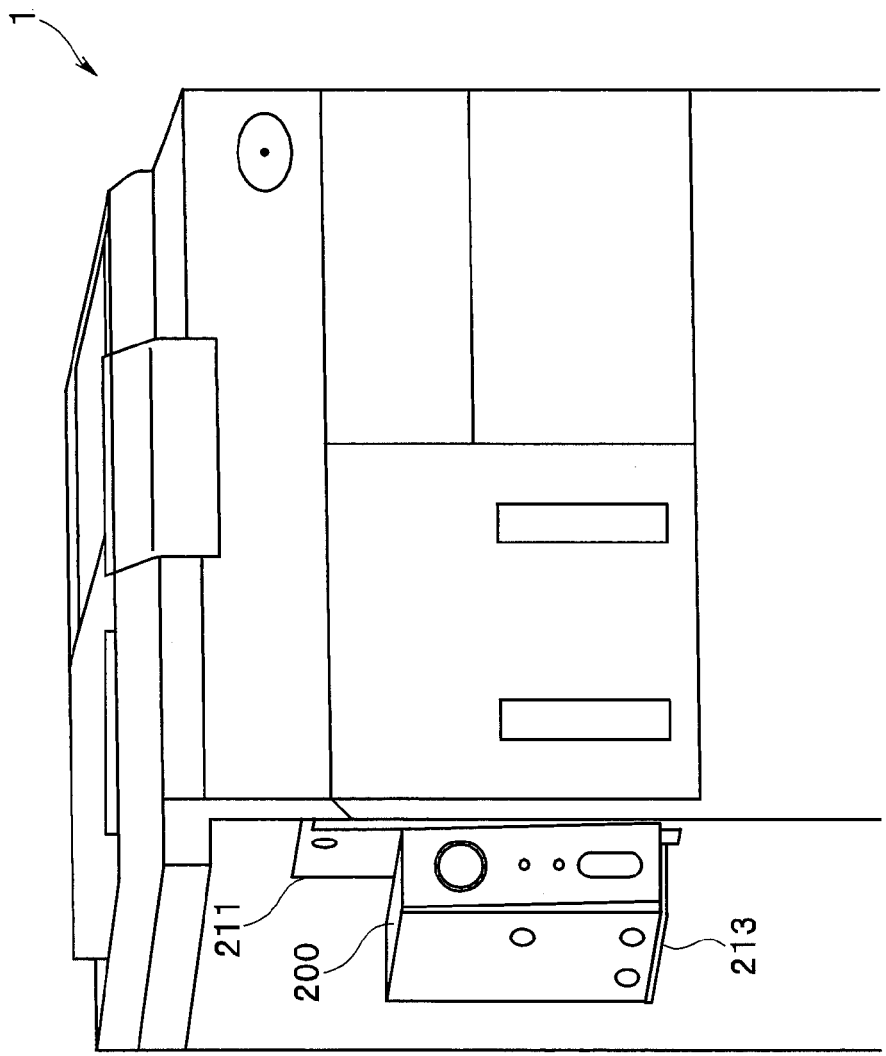
FIG. 32 is an enlarged diagram of FIG. 31 as obliquely viewed from the front.

FIG. 31 is a diagram showing a state in which a history management unit 200 is installed on each of opposite side faces of the cleaning/disinfecting apparatus 1, and FIG. 32 is an enlarged diagram of FIG. 31 as obliquely viewed from the front.

As illustrated in FIG. 31, a fixture 211 can be fixed to each of opposite side faces of the cleaning/disinfecting apparatus 1, and a history management unit 200 can be fixed to a bottom face 213 of each fixture 211. As described above, installing the history management units 200 on the side faces of the cleaning/disinfecting apparatus 1 enables space saving.

Figure 33:
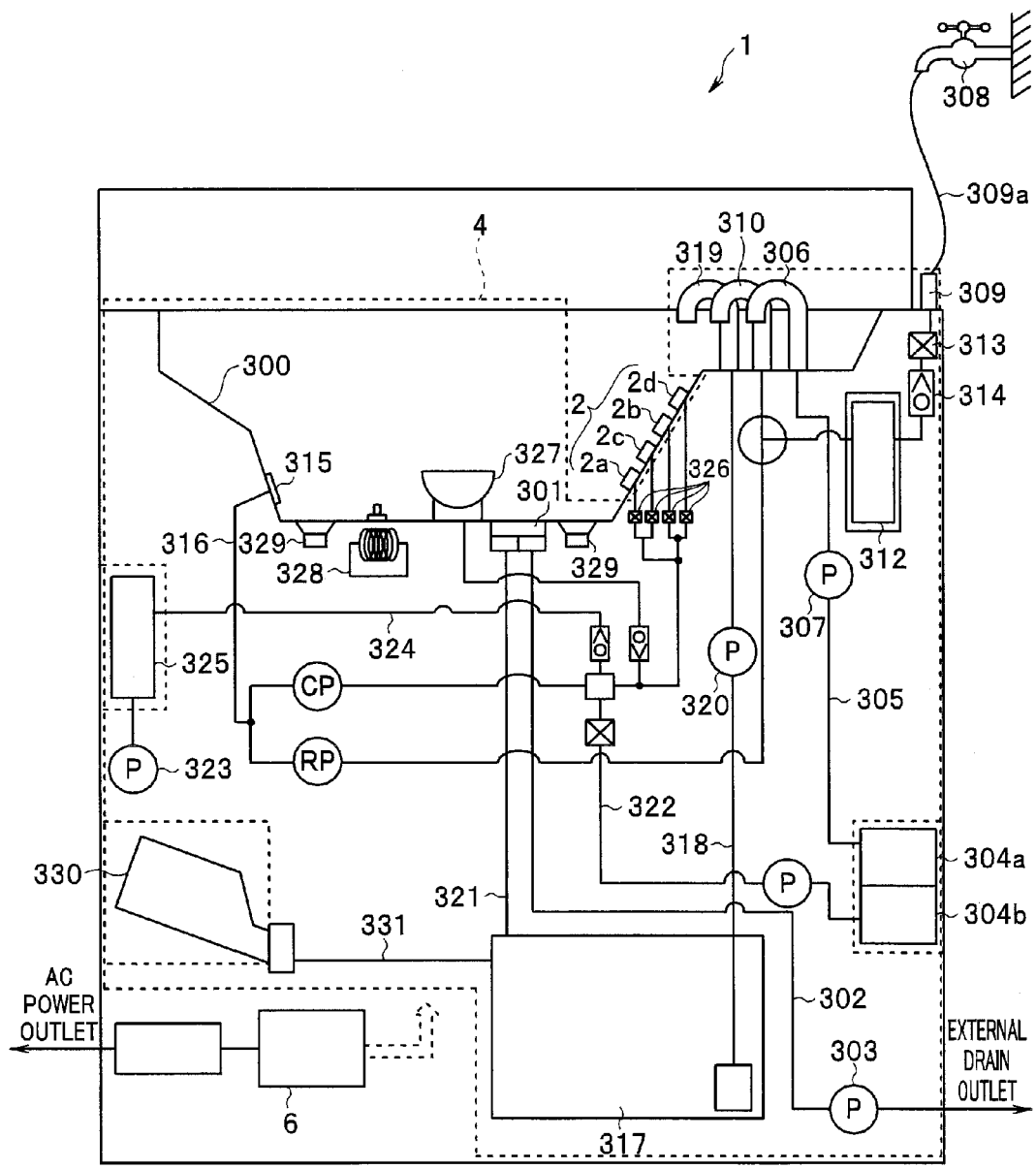
FIG. 33 is a diagram for conduit arrangement in a cleaning/disinfecting portion.

FIG. 33 is a conduit arrangement diagram showing an example of the cleaning/disinfecting portion 4.

For example, the cleaning/disinfecting portion 4 may include a basin-like cleaning bath 300 that enables endoscopes to be arranged therein, and the attachment portions 2 (2a, 2b, 2c and 2d) may be provided so as to open in the cleaning bath 300.

The cleaning/disinfecting portion 4 may include a drain outlet 301 provided so as to open in the cleaning bath 300, and a drain conduit 302 that links the drain outlet 301 and the outside of the apparatus. It is possible to provide a drain pump 303 in the drain conduit 302 to enable a liquid in the cleaning bath 300 to be actively discharged.

The cleaning/disinfecting portion 4 may include a cleaning tank 304a that retains a cleaning liquid for cleaning endoscopes, a detergent conduit 305 drawn from the cleaning tank 304a, a cleaning nozzle 306 that opens toward the cleaning bath 300, and a detergent pump 307 arranged in the detergent conduit 305, the detergent pump 307 sucking the cleaning liquid up from the cleaning tank 304a.

The cleaning/disinfecting portion 4 may include a water supply hose connection port 309 linked to a tap water faucet 308 and a water supply hose 309a outside the apparatus, a water supply circulation nozzle 310 that opens toward the cleaning bath 300, a water supply conduit 311 that links the water supply hose connection port 309 and the water supply circulation nozzle 310, a water supply filter 312 arranged in the water supply conduit 311, the water supply filter 312 filtrating tap water, a water supply solenoid valve 313 that adjusts supply of tap water from a water supply, and a check valve 314 that prevents reverse flow of tap water. For example, tap water can be used for cleaning liquid dilution, disinfecting liquid dilution or rinsing.

The cleaning/disinfecting portion 4 may include a circulation port 315 that opens in the cleaning bath 300, and a circulation conduit 316 that brings the circulation port 315 and the attachment portions 2 into communication with each other.

After supply of a cleaning liquid and tap water to the cleaning bath 300 for dilution of the cleaning liquid, the diluted cleaning liquid can be made flow through the circulation conduit 316 to introduce the cleaning liquid into endoscope conduits. However, the cleaning/disinfecting portion 4 according to the present invention is not limited to this example, and may have a structure in which the diluted cleaning liquid is made to flow directly from the cleaning tank 304a to the circulation conduit 316.

The cleaning/disinfecting portion 4 may include a chemical tank 317 that retains a disinfecting liquid, a chemical conduit 318 drawn from the chemical tank 317, a disinfecting liquid nozzle 319 that opens toward the cleaning bath 300, and a chemical pump 320 arranged in the chemical conduit 318, the chemical pump 320 sucking the disinfecting liquid up from the chemical tank 317.

As with the above-described cleaning liquid, the disinfecting liquid may be introduced to the endoscope conduits via the cleaning bath 300 or may be introduced directly from the chemical tank 317.

The chemical tank 317 may be connected to the drain outlet 301 via a chemical recovery conduit 321. A disinfecting liquid used for disinfecting endoscopes may be recovery in the chemical tank 317 and re-used for next disinfection.

The cleaning/disinfecting portion 4 may include an alcohol tank 304b that retains alcohol, and an alcohol conduit 322 that links the alcohol tank 304b and the attachment portions 2.

The cleaning/disinfecting portion 4 may include an air pump 323 that connects to the outside of the apparatus, and an air conduit 324 that links the air pump 323 and the attachment portions 2. The air conduit 324 may include an air filter 325 that filtrates air supplied by the air pump 323.

The air conduit 324 may be connected to conduits for supplying a cleaning liquid or a disinfecting liquid to the attachment portions 2 to enable a fluid mixed by a gas and a liquid to be supplied to the endoscopes.

A solenoid valve 326 may be provided in each of the attachment portions (2a, 2b, 2c and 2d) to adjust opening/closing of the solenoid valve 326 and a degree of opening of the solenoid valve 326 by means of the control portion 6, enabling a cleaning/disinfection menu to be varied. Also, a pump is provided in each of conduits linked to the respective attachment portions, enabling a cleaning menu to be varied according to an output from the pump.

The cleaning/disinfecting portion 4 may include a cleaning case 327 that receives endoscope accessories during cleaning and disinfection, a heater 328 that heats the cleaning bath 300, an ultrasound transducer 329 that performs ultrasound vibration of a liquid in the cleaning bath 300, and a chemical supply conduit 331 that connects an endoscope cleaning/ disinfecting chemical bottle 330 attached to a cleaning/disinfecting apparatus to the chemical tank 317.

REFERENCE EXAMPLE 1

In an endoscope cleaning/disinfecting apparatus, after an endoscope is cleaned and disinfected, an alcohol flush that feeds alcohol to internal conduits of the endoscope to precipitate drying can be performed. The alcohol flush can be performed following cleaning and disinfection by incorporating the alcohol flush in a cleaning/disinfection process. A certain amount of alcohol is sucked up from an alcohol tank housed in the endoscope cleaning/disinfecting apparatus and supplied.

If there is no required amount of alcohol in the alcohol tank, the endoscope cleaning/disinfecting apparatus detects lack of alcohol during an alcohol flush and makes an abnormal stop of the cleaning/disinfection process.

On the other hand, in recent years, the necessity of keeping a history of cleaning/disinfection records for endoscopes has been emphasized. An endoscope cleaning/disinfecting apparatus holds cleaning/disinfection process operation record data, which assists a user with endoscope cleaning and disinfection management. If alcohol insufficiency such as mentioned above occurs, operation record data indicating an "abnormal end" of a cleaning/disinfection process is left. In order to obtain operation record data indicating a "normal end", it is necessary to restart the entire cleaning/disinfection process from the beginning, which causes a lot of trouble.

Therefore, arrangement is made so that if a required amount of alcohol is not provided, the endoscope cleaning/disinfecting apparatus can temporarily stop the cleaning/disinfection process, give a warning to replenish an alcohol tank with alcohol, and resume the cleaning/disinfection process. Consequently, even if alcohol is insufficient, an alcohol flush can be completed without making an abnormal stop of the cleaning/disinfection process. In other words, it is possible to leave operation record data indicating a "normal end" of a cleaning/disinfection process without restarting the cleaning/disinfection process from the beginning.

REFERENCE EXAMPLE 2

An endoscope cleaning/disinfecting apparatus holds cleaning/disinfection process operation record data, and can print the operation record data using an incorporated dedicated printer. Contents to be printed include end times of cleaning/disinfection processes, contents of settings such as cleaning time period and disinfection time period, serials numbers of the cleaning/disinfecting apparatus and endoscopes to be cleaned/disinfected, user information and the number of operations of the cleaning/disinfecting apparatus. Where operation record data indicates an "abnormal end", an abnormality code indicating the content of the abnormality is printed in the contents.

However, since differences in printed contents between a "normal end" and an "abnormal end" are small, it is difficult to distinguish between a "normal end" and an "abnormal end".

Therefore, in order to make it easy to know a failure in a normal end, arrangement is made so that contents of settings such as "cleaning time period" and "disinfection time period" are deleted from the printed contents of an "abnormal end".

And, a cleaning/disinfection process start time is added to the printed contents in both of a "normal end" and an "abnormal end".

Consequently, printed contents of operation record data can easily be understood.

REFERENCE EXAMPLE 3

An endoscope cleaning/disinfecting apparatus holds cleaning/disinfection process operation record data, and the operation record data can be printed using an incorporated dedicated printer. After a normal end or an abnormal end of a cleaning/disinfection process for an endoscope, a print button included in the endoscope cleaning/disinfecting apparatus is pressed, whereby operation record data is printed by the printer.

If a user performs printing each time a cleaning/disinfection process ends, the frequency of pressing the print button is increased, which is a burden for the user.

Therefore, arrangement is made so that settings can be made to automatically print operation record data in synchronization with an end of a cleaning/disinfection process. Settings can also be made to prevent operation record data from being automatically printed.

Consequently, a work burden on the user can be reduced.

REFERENCE EXAMPLE 4

An endoscope cleaning/disinfecting apparatus holds cleaning/disinfection process operation record data, and can print the operation record data using an incorporated dedicated printer. As a result of printing being performed every time a cleaning/disinfection process ends, operation record data on all of the cleaning/disinfection processes can be outputted. Furthermore, a mode for collectively printing entire operation record data on cleaning/disinfection processes performed on that day is executed, enabling the operation record data to be printed chronologically.

However, in the aforementioned printing mode, only operation record data on "normally-ended" cleaning/disinfection processes are printed, and thus, collective printing cannot be performed which includes a status of generation of operation record data on "abnormal ends". Therefore, a user can acquire operation record data on an "abnormal end" only when a cleaning/disinfection process makes an abnormal stop, which is inconvenient from the perspective of history management.

Therefore, arrangement is made so that operation record data on both "normally-ended" and "abnormally-ended" cleaning/disinfection processes issued on that day can be printed chronologically in the aforementioned printing mode. Also, settings can be made so as not to include operation record data on "abnormal ends" as in conventional techniques.

Consequently, the ability of cleaning/disinfection history management for the endoscope cleaning/disinfecting apparatus is enhanced.

REFERENCE EXAMPLE 5

When an endoscope cleaning/disinfecting apparatus senses an abnormality for some reasons during a cleaning/disinfection process, the endoscope cleaning/disinfecting apparatus displays an abnormality code according to a state of the abnormality on an operation panel of the endoscope cleaning/disinfecting apparatus and makes an abnormal stop of the cleaning/disinfection process while providing an abnormality buzzer sound. Provision of the abnormality buzzer sound ends after a short period of time, and the display of the abnormality code on the operation panel is maintained. The display of the abnormality code is deleted from the operation panel by pressing any button on the operation panel or opening a cover of a cleaning bath that receives an endoscope, and the endoscope cleaning/disinfecting apparatus returns to a standby state.

If a user performs the aforementioned operation with no intension of deleting the abnormality code from the operation panel, the only means for the user to know the abnormality code during the cleaning/disinfection process is printing operation record data on the "abnormal end" by pressing a print button. If the user is not aware of the abnormal end, it is likely that even printing is not performed.

On the other hand, if a user misses the abnormality buzzer sound because of ambient noise, it takes long for the user to know the abnormal end of the cleaning/disinfection process, which may result in a decrease in work efficiency.

Therefore, arrangement is made so that when an abnormality occurs during a cleaning/disinfection process, an abnormality code displayed on an operation panel and an abnormality buzzer sound provided cannot be deleted or stopped unless a stop button on an operation panel is pressed.

Consequently, differences in apparatus state between a normal end and an abnormal end are made clear, enabling a user to easily recognize occurrence of an abnormality.

The present invention is not limited to the above-described embodiments, and various modifications, alterations and the like are possible without departing from the spirit of the present invention.

What is claimed is:

1. A cleaning/disinfecting apparatus comprising:
a first attachment portion for attaching to a first internal conduit to be cleaned/disinfected in a first endoscope;
a second attachment portion for attaching to a second internal conduit to be cleaned/disinfected in either the first endoscope or in a second endoscope;
a cleaning/disinfecting portion that communicates with the first attachment portion and the second attachment portion, and can execute different types of cleaning/disinfection menus for the respective first and second attachment portions simultaneously, corresponding to different cleaning/disinfecting requirements for the first and second internal conduits to be cleaned/disinfected;
a first conduit that connects the first attachment portion and the cleaning/disinfecting portion;
a first solenoid valve provided in the first conduit;
a second conduit that connects the second attachment portion and the cleaning/disinfecting portion;
a second solenoid valve provided in the second conduit;
an endoscope information reading portion that reads endoscope information from the first and/or second endoscopes to be cleaned/disinfected; and
a control portion configured to:
determine a cleaning/disinfection menu from among the cleaning/disinfection menus based on the endoscope information for each of the first and second internal conduits to be cleaned/disinfected, and
control the first solenoid valve and the second solenoid valve such that the determined cleaning/disinfection menu for each of the first and second internal conduits to be cleaned/disinfected can be executed simultaneously.

2. The cleaning/disinfecting apparatus according to claim 1, wherein
the control portion outputs attachment portion identifying information for identifying an attachment portion from among the first and second attachment portions for executing the determined cleaning/disinfection menu for each of the first and second internal conduits;
the cleaning/disinfecting apparatus further comprises a notifying portion that notifies the attachment portion identifying information outputted from the control portion,
the notifying portion is a display, and
the display displays a name or a position of the assigned attachment portion from among the first and second attachment portions.

3. The cleaning/disinfecting apparatus according to claim 1, wherein
the control portion outputs attachment portion identifying information for identifying an attachment portion from among the first and second attachment portions for executing the determined cleaning/disinfection menu for each of the first and second internal conduits,
the cleaning/disinfecting apparatus further comprising a notifying portion that notifies the attachment portion identifying information outputted from the control portion,
the notifying portion is a lighting portion installed in each of the first and second attachment portions, and
only the lighting portion installed in the assigned attachment portion from among the first and second attachment portions illuminates or blinks.

4. The cleaning/disinfecting apparatus according to claim 1, wherein
the control portion identifies an attachment portion among the first and second attachment portions for executing the determined cleaning/disinfection menu for each of the first and second internal conduits,
the cleaning/disinfection apparatus further comprising a connection sensing portion for sensing that the first and second internal conduits are connected to the attachment portion from among the first and second attachment portions;
the control portion determines, based on a sensing result from the connection sensing portion, whether or not the first and second internal conduits are connected to the assigned attachment portion from among the first and second attachment portions; and
if the control portion determines that the first and second internal conduits are connected to the attachment portion from among the first and second attachment portions to which the cleaning/disinfection menu is not assigned, an error is notified by a notifying portion.

* * * * *